US012668798B2

(12) United States Patent
Shiba et al.

(10) Patent No.: US 12,668,798 B2
(45) Date of Patent: Jun. 30, 2026

(54) ANTISENSE NUCLEIC ACID TARGETING APOC3

(71) Applicants: NATIONAL CEREBRAL AND CARDIOVASCULAR CENTER, Suita (JP); OSAKA UNIVERSITY, Suita (JP)

(72) Inventors: Mariko Shiba, Suita (JP); Tsuyoshi Yamamoto, Suita (JP); Fumito Wada, Suita (JP); Tadayuki Kobayashi, Suita (JP); Keisuke Tachibana, Suita (JP); Satoshi Obika, Suita (JP)

(73) Assignees: NATIONAL CEREBAL AND CARDIOVASCULAR CENTER, Suita (JP); OSAKA UNIVERSITY, Suita (JP)

( * ) Notice: Subject to any disclaimer, the term of this patent is extended or adjusted under 35 U.S.C. 154(b) by 831 days.

(21) Appl. No.: 17/907,323

(22) PCT Filed: Mar. 26, 2021

(86) PCT No.: PCT/JP2021/013106

§ 371 (c)(1),
(2) Date: Sep. 26, 2022

(87) PCT Pub. No.: WO2021/193965

PCT Pub. Date: Sep. 30, 2021

(65) Prior Publication Data

US 2023/0113556 A1 Apr. 13, 2023

(30) Foreign Application Priority Data

Mar. 26, 2020 (JP) ................................ 2020-055717

(51) Int. Cl.
*C07H 21/02* (2006.01)
*A61P 3/06* (2006.01)
*C07H 21/04* (2006.01)
*C12N 15/113* (2010.01)

(52) U.S. Cl.
CPC .............. *C12N 15/113* (2013.01); *A61P 3/06* (2018.01)

(58) Field of Classification Search
CPC .......................... C12N 15/113; C12N 2310/11
See application file for complete search history.

(56) References Cited

U.S. PATENT DOCUMENTS

2015/0126719 A1 5/2015 Prakash et al.
2021/0198305 A1* 7/2021 Vargeese ................ C07H 17/04
2022/0160880 A1 5/2022 Harada-Shiba et al.

FOREIGN PATENT DOCUMENTS

JP 2016-526874 A 9/2016
WO WO 2004/093783 A2 11/2004
WO WO-2006042418 A1 * 4/2006 .............. A61P 31/12
WO WO2014/179626 A2 * 11/2014 ........... C12N 15/113
WO WO-2016138278 A2 * 9/2016 ......... A61K 31/7105
WO WO 2018/216785 A1 11/2018
WO 2018/223056 A1 12/2018

OTHER PUBLICATIONS

Alnylam Pharmaceuticals (Alnylam Pharmaceuticals, 2013, 1-3).*
Stein (The Journal of Clinical Investigation, 2001, 108, 5, 641-644).*
Nedorezova et al. (Theranostics, 2022, vol. 12, Issue 16, 7132-7157).*
Japan Patent Office, International Search Report in International Application No. PCT/JP2021/013106 (Apr. 20, 2021).
Schmitz et al., "APOC-III Antisense Oligonucleotides: A New Option for the Treatment of Hypertriglyceridemia," Curr. Med. Chem., 25(13): 1567-1576 (2018).
Vahdat Lasemi et al., "Harnessing Nucleic Acid-Based Therapeutics for Atherosclerotic Cardiovascular Disease: State of the Art," Drug Discov. Today, 24(5): 1116-1131 (2019).
Yamamoto et al., "Locked Nucelic Acid Antisense Inhibitor Targeting Apolipoprotein C-III Efficiently and Preferentially Removes Triglyceride from Large Very Low-Density Lipoprotein Particles in Murine Plasma," Eur. J. Pharmacol., 723: 353-359 (2014).
European Patent Office, Communication pursuant to Rule 164(1) EPC in European Patent Application No. 21775328.4 (Jun. 13, 2025).
Straarup et al., "Short Locked Nucleic Acid Antisense Oligonucleotides Potently Reduce Apolipoprotein B mRNA and Serum Cholesterol in Mice and Non-human Primates," Nucleic Acids Res., 38(20): 7100-7111 (2010).

* cited by examiner

*Primary Examiner* — Amy Rose Hudson
(74) *Attorney, Agent, or Firm* — Leydig, Voit & Mayer, Ltd.

(57) ABSTRACT

The present invention provides an antisense oligomer having the base sequence depicted in SEQ ID NO: 26, an antisense oligomer having a base sequence resulting from substitution, deletion, insertion, or addition of 1 to 6 bases in the base sequence depicted in SEQ ID NO: 26, a pharmaceutically acceptable salt thereof, or a pharmaceutically acceptable hydrate thereof, an oligonucleotide conjugate in which the antisense oligomer is bound with a molecule capable of binding to an asialoglycoprotein receptor, and a pharmaceutical composition containing the same.

10 Claims, 9 Drawing Sheets

Specification includes a Sequence Listing.

ANTISENSE NUCLEIC ACID TARGETING APOC3

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 11,652 Byte ASCII (Text) file named "764866_ST25.txt," created on Sep. 22, 2022.

TECHNICAL FIELD

This invention relates to an antisense nucleic acid targeting APOC3, and a pharmaceutical composition containing the same.

BACKGROUND ART

Causal correlation between lipid and atherosclerosis has been clinically established by the finding of statin and drug intervention trials using the same. The effect of statin on the reduction of low density lipoprotein-cholesterol (LDL-C) is potent and, irrespective of background risk factors, the risk of cardiovascular events is certainly reduced by the reduction of a certain amount of LDL-C. On the other hand, it has become a problem how to solve "residual risks" that cannot be solved by statin.

Mendelian randomization (MR) studies have revealed that causative genes of hypercholesterolemia and hypertriglyceridemia also cause atherosclerosis, which strongly suggests that a key of the residual risks rests in these hyperlipidemias. Concomitantly, drug discovery studies targeting these causative genes have also been developed.

For example, WO 2018-216785 (Patent Literature 1) describes antisense nucleic acids targeting PCSK9, which is one of the causative genes of hypercholesterolemia, and medicaments containing the same. The antisense nucleic acids described in this patent literature are gapmer type nucleic acids that have modified nucleic acids consisting of several bases at both sides.

Besides, WO 2004-093783 (Patent Literature 2) describes antisense oligonucleotides (ASOs) targeting apolipoprotein C3 (APOC3), which is one of the causative genes of hypertriglyceridemia. Hypertriglyceridemia is one of hyperlipidemias in which blood TG value shows 150 mg/dL or more. APOC3 is involved in clearance of lipoproteins by playing multifaceted roles therein, such as inhibition of uptake of lipoproteins into the liver and inhibition of lipoprotein lipase (LPL). It has epidemiologically been shown that people having reduced function or a loss-of-function type mutation of APOC3 have a low risk of blood TG value and coronary heart diseases, and APOC3 is considered as a good drug discovery target for hypertriglycergidemia.

Patent Literature 2 describes ASO having a "5-10-5" type gapmer structure that is constituted of a central gap region consisting of 10 DNAs and 5'- and 3'-wing regions each consisting of 5 nucleotides and adjacent to the both ends of the region, wherein the nucleotides in the both wing regions are 2'-O-methoxyethyl (2'-MOE) modified, and all internucleoside bonds are substituted with phosphorothioate (PS) bonds. An APOC3 inhibitor volanesorsen (trade name: Waylivra (registered trade mark)) containing (ISIS 304801) as an active ingredient disclosed in this patent application has been shown to be effective to patients suffering from hyperchylomicronemia including LPL deficiency, and expected as a new therapeutic drug for primary hypertriglyceridemia and more common atherosclerosis-inducing hypertriglyceridemia. However, serious adverse events due to high dose administration were reported, Food and Drug Administration (FDA) refused the application for approval from the aspects of safety, and European Medicines Agency (EMA) conditionally approved only for familial hyperchylomicronemia.

Therefore, it has been desired to develop a novel nucleic acid drug that can inhibit APOC3 expression at lower doses and can be widely and safely used for atherosclerosis-inducing hyperlipemia.

CITATION LIST

Patent Literature

[PTL 1]
WO 2018-216785
[PTL 2]
WO 2004-093783

SUMMARY OF INVENTION

Technical Problem

An invention described in this specification aims to provide an antisense nucleic acid targeting APOC3 that allows reduction of dose due to its high activity, a conjugate containing the antisense nucleic acid, and a medicament containing the same.

Solution to Problem

The present inventors designed ASOs complimentary to 5'-UTR, coding region, and 3'-UTR of APOC3 mRNA, synthesized the ASOs wherein a part of their constituent nucleotides is modified by a bridge between the 2'-position and the 4'-position of the sugar, and introduced them into cultured cells. As a result, the present inventors found that, among these ASOs, ASOs complimentary to a specific region of APOC3 mRNA have a remarkably superior inhibitory activity against APOC3 gene expression. When the target region overlaps with the sequence described in Patent Literature 2, the ASOs having 2',4'-bridge modifications showed APOC3 expression inhibitory activities higher than those of ASOs having 2'-MOE modifications.

In addition, as shown in Examples, in vivo administration of an antisense oligomer having the base sequence depicted in SEQ ID NO: 26, an antisense oligomer having a base sequence resulting from substitution, deletion, insertion or addition of 1 to 6 bases in the base sequence depicted in SEQ ID NO: 26, or a conjugate thereof, to a non-human primate resulted in high APOC3 expression inhibitory activity and blood TG value-reducing action, without causing adverse events.

The present inventors reached completion of the present invention with further investigation based on these findings.

Advantageous Effects of Invention

This specification can provide an antisense nucleic acid targeting APOC3 that allows reduction of dose due to its high activity, a conjugate thereof, and a medicament containing the same.

BRIEF DESCRIPTION OF DRAWINGS

FIG. 4*a* shows the effect on residual mouse hepatocytes in human liver chimeric mice, and FIG. 4*b* shows the effect on human hepatocytes in human liver chimeric mice.

DESCRIPTION OF EMBODIMENTS

Figure 1:
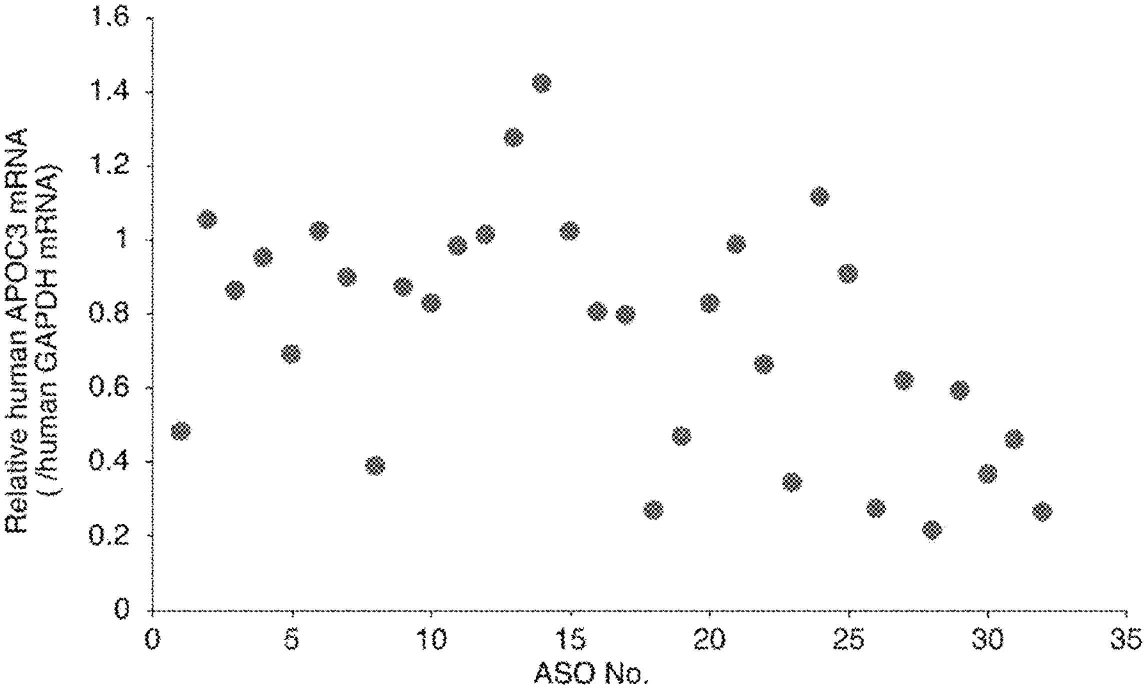
FIG. 1 shows the results of the first in vitro screening for antisense nucleic acids targeting human APOC3 mRNA using CEM method.

Hereinafter, embodiments to carry out the present invention are described. The present invention is not limited to the embodiments described below, and encompasses those appropriately modified within the scope obvious to those of ordinary skill in the art from the following embodiments.

Antisense Nucleic Acid

The first invention described in this specification relates to an antisense oligomer, a pharmaceutically acceptable salt thereof, or a pharmaceutically acceptable hydrate thereof (hereinafter also collectively referred to as the antisense nucleic acid of the present invention).

The length of the base sequence of the oligonucleotide (antisense oligomer) used in the present invention is not particularly limited. The length of the base sequence of the antisense oligomer may be, for example, any of 10 to 25 bases, 12 to 22 bases, 13 to 21 bases, 14 to 20 bases, 13 to 16 bases (14 to 16 bases), 13 to 15 bases (14 or 15 bases), or 14 bases.

Examples of the pharmaceutically acceptable salt of the antisense oligomer include salts composed of inorganic base, ammonia, organic base, inorganic acid, halogen ion (Cl, etc.), and intramolecular salts. Examples of the inorganic base include alkali metals (Na, K, etc.) and alkaline earth metals (Ca, Mg, etc.). Examples of the organic base include trimethylamine, triethylamine, choline, procaine, ethanolamine, and the like. Examples of the inorganic acid include hydrochloric acid, hydrobromic acid, sulfuric acid, nitric acid, phosphoric acid, and the like. The pharmaceutically acceptable hydrate of the antisense oligomer may be any hydrate.

Examples of the antisense oligomer in the antisense nucleic acid of the present invention include an antisense oligomer having the base sequence depicted in SEQ ID NO: 26, an antisense oligomer having a base sequence resulting from substitution, deletion, insertion or addition of 1 to 6 bases in the base sequence depicted in SEQ ID NO: 26, a pharmaceutically acceptable salt thereof, or a pharmaceutically acceptable hydrate thereof. The base sequences specified by SEQ ID NOs also include linear and cyclic ones. Examples of the constitutional unit of the antisense oligomer in the antisense nucleic acid of the present invention include ribonucleotide (RNA) and deoxyribonucleotide (DNA). These nucleotides may be modified or unmodified.

The aforementioned nucleotide residue contains sugar, base, and phosphate as constituent elements. Ribonucleotide has a ribose residue as sugar and adenine (A), guanine (G), cytosine (C), 5-methylcytosine (mC), or uracil (U) (which can also be replaced by thymine (T)) as a base.

Deoxyribonucleotide residue has a deoxyribose residue as sugar and adenine (dA), guanine (dG), cytosine (dC), 5-methylcytosine (dmC), or thymine (dT) (which can also be replaced by uracil (dU)) as a base. In the following, nucleotides having adenine, guanine, (5-methyl)cytosine, uracil, and thymine may be respectively referred to as adenine nucleotide, guanine nucleotide, (5-methyl)cytosine nucleotide, uracil nucleotide, and thymine nucleotide.

Preferred examples of the antisense oligomer having a base sequence resulting from substitution, deletion, insertion or addition of 1 to 6 bases in the base sequence depicted in SEQ ID NO: 26 are an antisense oligomer having the base sequence depicted in any of SEQ ID NOs: 26 and 37 to 41, and an antisense oligomer having a base sequence resulting from substitution, deletion, insertion or addition of 1 or 2 bases in the base sequence depicted in any of SEQ ID NOs: 26 and 37 to 41. Of these, an antisense oligomer having the base sequence depicted in SEQ ID NO: 26 is more preferred.

SEQ ID NO: 26: agaatactgtccct
SEQ ID NO: 37: tgagaatactgtccct
SEQ ID NO: 38: gagaatactgtccct
SEQ ID NO: 39: agaatactgtccctt
SEQ ID NO: 40: tgagaatactgtccctt
SEQ ID NO: 41: actgagaatactgtcccttt Preferred examples of the antisense nucleic acid of the present invention include an antisense oligomer that is complementary to the human apolipoprotein C3 (APOC3) gene, has activity to inhibit the expression of the APOC3 gene, and is an oligonucleotide, a pharmaceutically acceptable salt thereof, and a pharmaceutically acceptable hydrate thereof. This antisense nucleic acid can bind to the APOC3 gene. Preferably, this antisense nucleic acid can form a double-stranded nucleic acid with the APOC3 gene. This antisense nucleic acid binds to the APOC3 gene and has the activity of degrading APOC3 mRNA or inhibiting the biosynthesis of APOC3 protein. The activity thereof can be evaluated using, for example, the CEM method as shown in the Examples below.

The human APOC3 gene has the base sequence depicted in SEQ ID NO: 33, and encodes the amino acid sequence depicted in SEQ ID NO: 34. The human APOC3 gene includes not only those having the base sequence depicted in SEQ ID NO: 33 but also variants occurring in a living human body, and also includes those having a base sequence resulting from substitution, deletion, insertion or addition of 1 to several (2, 3, 4, 5, or 6) bases in the base sequence depicted in SEQ ID NO: 33. The binding site of the antisense nucleic acid of the present invention with the human APOC3 gene can be confirmed using a known method.

A preferred example of the antisense nucleic acid of the present invention has a modification site in which either or both of the sugar moiety and the phosphate bond moiety of at least one nucleotide constituting the oligonucleotide are modified.

A preferred example of the antisense nucleic acid of the present invention has a first modification site in which the sugar moiety of at least one nucleotide constituting the oligonucleotide is modified in a region from 2 to 7 bases from the 5' end, and a second modification site in which the sugar moiety of at least one nucleotide constituting the oligonucleotide is modified in a region from 2 to 4 bases from the 3' end.

Having such modifications, the antisense nucleic acid is not easily degraded by nucleases and can exist in vivo for a long time after administration.

Known modifications can be employed as appropriate. An example of the modification is a bridge structure between the 4'-position and the 2'-position. Examples of the bridge structure are α-L-methyleneoxy, @-D-methyleneoxy, and ethyleneoxy. Other examples of the bridge structure include oxyamino (4'-$CH_2$—NH—O-2'), N-methyloxyamino (4'-$CH_2$—$NCH_3$—O-2'), unsubstituted amide (4'-CO—NH-2'), N-methylamide (4'-CO—$NCH_3$-2'), acetamide (4'-$CH_2$—CO—NH-2'), N-methylacetamide (4'-$CH_2$—CO—$NCH_3$-2'), N-oxyacetamide (4'-$CH_2$—CO—NH—O-2'), and N-methyl-N-oxyacetamide (4'-$CH_2$—CO—$NCH_3$—O-2'). These can be synthesized by the method described in WO2011/052436 or WO2012/029870.

Other examples of the bridge structure include amino (4'-$CH_2$—NH-2') and N-methylamino (4'-CH—$NCH_3$-2'). These can be synthesized by the method described in, for example, Kumar R. et al., Bioorg. & Med. Chem. Lett., 1998, 8, 2219-2222; Singh S. K. et al., J. Org. Chem., 1998, 63, 10035-39.

These bridge structures are introduced into nucleosides constituting oligonucleotides to form bridged nucleosides. When multiple bridged nucleosides are present in the oligonucleotide, the bridge structures may all be the same or different, and they are not particularly limited. The content ratio of the bridged nucleoside in the oligonucleotide is not particularly limited. An example of the lower limit is 5% by number, 7% by number, 10% by number, 15% by number, 20% by number, or 25% by number, and an example of the upper limit is 100% by number, 90% by number, 80% by number, 70% by number, or 60% by number.

At least one nucleotide at the first modification site and the second modification site preferably has a modified sugar including 2'-modification. As the 2'-modification, a known 2'-modification may be employed as appropriate. The 2'-modification may be a bridge structure between the 4'-position and the 2'-position. These can be synthesized, for example, by the method described in WO 2011/052436.

An example of 2'-modification in the modified sugar including 2'-modification is 2'-OMe or 2'-$OCH_2CH_2OMe$ wherein Me is a methyl group, or the modified sugar including 2'-modification is a locked nucleic acid sugar (LNA) (sugar modified with a group represented by —O—$CH_2$— between $C_2$ and $C_4$ of the sugar moiety).

Alternatively, an example of the 2'-modification in the modified sugar including 2'-modification is 2'-F (fluoro).

Alternatively, the modified sugar including 2'-modification is AmNA (sugar modified with a group represented by —N($CH_3$)—CO— between $C_2$ and $C_4$ of the sugar moiety).

In addition, at least one nucleotide in the first modification site and the second modification site may be a non-modified nucleotide (RNA or DNA).

In the sugar-phosphate backbone, for example, a phosphate group can be modified. In the aforementioned sugar-phosphate backbone, a phosphate group at the closest adjacency to the sugar residue is called an "α-phosphate group". The aforementioned α-phosphate group is charged negatively, and the electric charges are distributed evenly over two oxygen atoms that are not linked to the sugar residue. Among the four oxygen atoms in the aforementioned α-phosphate group, the two oxygen atoms not linked to the sugar residue in the phosphodiester linkage between the nucleotide residues are hereinafter referred to as "non-linking oxygens". On the other hand, two oxygen atoms that are linked to the sugar residue in the phosphodiester linkage between the aforementioned nucleotide residues are hereinafter referred to as "linking oxygens". For example, the aforementioned α-phosphate group is preferably modified to be uncharged, or to render the charge distribution in the aforementioned non-linking oxygen asymmetric.

In the aforementioned phosphate group, for example, the aforementioned non-linking oxygen(s) may be substituted. The aforementioned oxygen(s) can be substituted with, for example, any atom selected from S (sulfur), Se (selenium), B (boron), C (carbon), H (hydrogen), N (nitrogen), and OR (R is an alkyl group or an aryl group) and substitution with S is preferred. Either one or both of the aforementioned non-linking oxygens may be substituted, and it is preferable that either one or both of the non-linking oxygens be substituted with S. More specifically, as the aforementioned modified phosphate group, for example, phosphorothioates, phosphorodithioates, phosphoroselenates, boranophosphates, boranophosphate esters, hydrogen phosphonates, phosphoroamidates, alkyl or aryl phosphonates, phosphotriesters, and the like can be mentioned.

In the antisense nucleic acid of the present invention having a modification in the phosphate bond moiety, for example, the phosphate bond moiety of at least one nucleotide is any one selected from the group consisting of phosphorothioate bond, phosphorodithioate bond, alkylphosphonate bond, phosphoramidate bond, and boranophosphate bond. Among these modifications in phosphate bond moieties, the phosphorodithioate bond is preferred.

The aforementioned phosphate group may be substituted with a phosphorus-free linker. The aforementioned linker may be siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo, methyleneoxymethylimino, or the like. Preferably, the linker may be a methylenecarbonylamino group or a methylenemethylimino group. Alternatively, the 25 aforementioned phosphate group may also be substituted with another phosphate-free linker. Examples of such linker include those described in "Med. Chem. Commun., 2014, 5, 1454-1471" and the like.

In a preferred embodiment, ½ or more, more preferably ⅔ or more, of the phosphate group is modified by one or more of the above-mentioned phosphate groups, and further preferably all phosphate groups are modified. For example, in the case of 15 mer antisense nucleic acid, 8 or more, preferably 10 or more, more preferably all phosphate groups, are, for example, phosphorothioated, phosphorodithioated, or the like. Substitution of unbound oxygen at the phosphoric diester bond with sulfur atom is important in the improvement of nuclease resistance and the tissue distribution of antisense nucleic acid.

Among the antisense oligomers having the base sequence depicted in any of the above-mentioned SEQ ID NOs: 26 and 37-41, the following No. 26-1 (sometimes simply indicated as "No. 26") to No. 26-6 are preferred. These may be subjected to the aforementioned substitution, deletion, insertion, or addition, or further modification.

No. 26-1: (SEQ ID NO: 26)
AGAatactgtcCCt

No. 26-2: (SEQ ID NO: 37)
TgAgAatactgtcCCt

No. 26-3: (SEQ ID NO: 38)
GAgAatactgtcCCt

No. 26-4: (SEQ ID NO: 39)
AGAatactgtccCTt

No. 26-5: (SEQ ID NO: 40)
TgAgAatactgtccCTt

No. 26-6: (SEQ ID NO: 41)
AcTgagAatactgtcccTtT

Other preferred antisense oligomers having the base sequence depicted in SEQ ID NO: 38 are the following No. 26-7 to No. 26-13. These may also be subjected to the aforementioned substitution, deletion, insertion, or addition, or further modification.

No. 26-7: (SEQ ID NO: 38)
GAG$^R$AatactgtcCCt

No. 26-8: (SEQ ID NO: 38)
GAG$^F$AatactgtcCCt

No. 26-9: (SEQ ID NO: 38)
GAGAatactgtcCCt

No. 26-10: (SEQ ID NO: 38)
GAG$^F$A$^R$atactgtcCCt

No. 26-11: (SEQ ID NO: 38)
GA$^R$GAatactgtcCCt

-continued

No. 26-12: (SEQ ID NO: 38)
GA$^F$GAatactgtcCCt

No. 26-13: (SEQ ID NO: 38)
GAGAatactgtcCCt wherein upper-case letters indicate LNA (Locked Nucleic Acid) (C is 5-methylcytosine LNA),
lower-case letters indicate DNA,
upper-case letters+underline indicates 2'-O-Me modification,
$N^R$ indicates RNA (2'-OH) ("N" indicates any base, hereinafter the same),
$N^F$ indicates 2'-Fluoro modification, and
each internucleoside bond indicates phosphorothioate bond.

In another preferred embodiment, the present invention provides a single-stranded oligonucleotide that inhibits APOC3 gene expression, which oligonucleotide contains a nucleotide sequence complementary to a sequence of continuous 10 or more nucleotides in a target region consisting of any nucleotide sequence selected from the group consisting of 438th-526th, 361st-381st, and 333rd-351st, nucleotide sequences in a nucleic acid encoding APOC3 and consisting of the nucleotide sequence represented by SEQ ID NO: 33,
the aforementioned single-stranded oligonucleotide has a length of 10 to 25 nucleotides, and
a sugar moiety of at least one nucleoside constituting the aforementioned single-stranded oligonucleotide is modified by a bridge between the 2'-position and the 4'-position of sugar moiety.

Here, the "single-stranded oligonucleotide" encompasses not only a free form but also a pharmaceutically acceptable salt thereof or a pharmaceutically acceptable hydrate thereof. The pharmaceutically acceptable "salt" and "hydrate" are as defined above.

In the present specification, the "antisense oligonucleotide (ASO)" means a single-stranded oligonucleotide that specifically hybridizes to a sequence consisting of 10 or more continuous nucleotides in a target nucleic acid. In addition, "inhibiting APOC3 gene expression" is used to encompass any embodiment in which the expression level of APOC3 protein is reduced and the activity of APOC3 is reduced as a result of contact of ASO with the cell, as compared with the case of no contact. For example, it includes degradation of target RNA by RNase H (e.g., by gapmer) and inhibition of protein synthesis by specific and stable hybridization with target RNA. The degree of inhibition of the expression is not particularly limited as long as it is statistically significant. For example, when the expression level of APOC3 mRNA or protein is reduced by 20% or more, preferably 50% or more, more preferably 75% or more, compared with the case of no contact between the cell and ASO, the ASO is considered to have APOC3 gene expression inhibitory activity.

Specifically, the ASO of the present invention targets a region consisting of any nucleotide sequence selected from the group consisting of 438th-526th, 361st-381st, and 333rd-351st, nucleotide sequences in APOC3 mRNA ("t" is read as "u" in the nucleotide sequence) consisting of the nucleotide sequence represented by SEQ ID NO: 33, and contains a nucleotide sequence complementary to a sequence of continuous 10 or more nucleotides in the region.

As used herein, "complementary" means not only a sequence that is completely complementary to the target sequence (that is, hybridizes without mismatch), but also a sequence containing mismatch of one to several (e.g. 1, 2, 3, 4, 5) nucleotides, preferably 1 or 2 nucleotides, as long as it can hybridize with APOC3 mRNA under physiological conditions of human cells. For example, a sequence having an identity of 90% or more, preferably 95% or more, 96% or more, 97% or more, 98% or more, 99% or more, most preferably 100%, to a complementary strand sequence of the target nucleotide sequence in APOC3 mRNA can be mentioned. The "identity of nucleotide sequence" in the present invention can be calculated using the homology calculation algorithm NCBI BLAST (National Center for Biotechnology Information Basic Local Alignment Search Tool) under the following conditions (expectancy=10; gap allowed; filtering=ON; match score=1; mismatch score=−3). In addition, the complementarity of individual bases is not limited to the formation of Watson-Crick base pairs with target bases, and also includes formation of Hoogsteen base pairs and Wobble base pairs.

Alternatively, the "complementary nucleotide sequence" is a nucleotide sequence that hybridizes with the target sequence under stringent conditions. As used herein, the "stringent conditions" refers to, for example, the conditions described in Current Protocols in Molecular Biology, John Wiley & Sons, 6.3.1-6.3.6, 1999, for example, hybridization at 6×SSC (sodium chloride/sodium citrate)/45° C., followed by one or more times of washing at 0.2×SSC/0.1% SDS/50-65° C., and the like. Those of ordinary skill in the art can appropriately select hybridization conditions that afford equivalent stringency.

In a preferred embodiment, the region in APOC3 mRNA targeted by the ASO of the present invention is a region composed of any nucleotide sequence selected from the group consisting of 438th-451st, 448th-461st, 498th-511th, 513th-526th, 368th-381st, and 333rd-346th, nucleotide sequences in the nucleotide sequence represented by SEQ ID NO: 33, and a nucleotide sequence in the vicinity thereof. As used herein, the "nucleotide sequence in the vicinity thereof" means a nucleotide sequence of 10 nucleotides or less, preferably 5 nucleotides or less, adjacent to the above-mentioned 5'- and 3'-ends of each region defined by nucleotide numbers. The same 25 applies to the following.

In a more preferred embodiment, the region in APOC3 mRNA targeted by the ASO of the present invention is a region composed of the 438th-451st nucleotide sequence in the nucleotide sequence represented by SEQ ID NO: 33, and a nucleotide sequence in the vicinity thereof. As one preferred embodiment of the ASO of the present invention, which targets this region, an antisense oligomer having a base sequence depicted in any of SEQ ID NOs: 26 and 37 to 41, more specifically, the above-mentioned antisense nucleic acid No. 26-1 to No. 26-13, can be mentioned.

The ASO of the present invention targets a sequence consisting of 10 or more (e.g., 10, 11, 12, 13, 14, 15, 16, 17, 18, 19, 20), preferably 14 or more (e.g., 14, 15, 16, 17, 18, 19, 20), continuous nucleotides in any of the target regions mentioned above, and contains a nucleotide sequence complementary thereto.

As described above, the constitutional unit of the ASO of the present invention is, for example, optionally modified or non-modified RNA or DNA. Examples of RNA and DNA residues, and examples of modified nucleotide residues are as described above.

The ASO of the present invention is characterized in that the sugar moiety of at least one nucleoside is modified by a bridge between the 2'-position and the 4'-position of the sugar. The 2',4'-bridge modification can increase the binding force to the target RNA and in vivo metabolic stability (nuclease resistance) by the bridged structure thereof. Among the above-mentioned bridged nucleic acids, LNA, AmNA, GuNA, and scpBNA are more preferred. Preferably, the ASO of the present invention contains two or more (e.g., 2, 3, 4, 5 or more) bridged nucleic acid residues. The position of the bridged nucleic acid residue is not particularly limited as long as it does not show an adverse effect on the APOC3 expression inhibitory activity. For example, when the ASO of the present invention is of the below-mentioned gapmer-type, in one preferred embodiment, all or a part of the nucleotide residues in the wing region are/is modified by bridged nucleic acid.

The ASO of the present invention can include, in addition to the sugar moiety bridged modification described above, other sugar moiety modification, phosphate bond moiety modification, and base moiety modification. Examples of such modifications include those similar to the modifications described above.

In the ASO of the present invention, preferred examples of ASO targeting the region composed of any nucleotide sequence selected from the group consisting of 448th-461st, 498th-511th, 513th-526th, 368th-381st, and 333rd-346th, nucleotide sequences in the nucleotide sequence represented by SEQ ID NO: 33, and a nucleotide sequence in the vicinity thereof include those having the following nucleotide sequences:

```
SEQ ID NO: 28:
gagagcactgagaa (target sequence: 438-451)

SEQ ID NO: 30:
tattgggaggccag (target sequence: 498-511)

SEQ ID NO: 32:
cttcttgtccagct (target sequence: 513-526)

SEQ ID NO: 23:
atggataggcaggt (target sequence: 368-381)

SEQ ID NO: 18:
caggcagccacggc (target sequence: 333-346).
```

In a preferred embodiment, as ASO containing the nucleotide sequence shown in any of SEQ ID NOs: 28, 30, 32 and 23, the following can be mentioned.

```
SEQ ID NO: 28:
GAGagcactgaGAa

SEQ ID NO: 30:
TATtgggaggcCAg

SEQ ID NO: 32:
CTTcttgtccaGCt

SEQ ID NO: 23:
ATGgataggcaGGt

SEQ ID NO: 18:
CAGgcagccacGGc
```

wherein upper-case letters indicate LNA (Locked Nucleic Acid) (C is 5-methylcytosine LNA), lower-case letters indicate DNA, and each internucleoside bond indicates a phosphorothioate bond.

In a preferred embodiment, the ASO of the present invention is a gapmer-type nucleic acid containing (1) 5'-wing region located in 5'-end;
(2) 3'-wing region located in 3'-end; and
(3) a deoxy gap region located between region (1) and region (2). The gapmer-type ASO is a nucleic acid having DNA (deoxy gap region) and nucleic acid (wing region) introduced with modification and bridge on both sides thereof. With the DNA strand as the main strand, a target RNA complementary to the main strand and a heteroduplex nucleic acid are formed, and the target RNA is degraded by RNase H endogenously existing in the cell. The constituent nucleotide of the wing region may be RNA or DNA.

The 5'- and 3'-wing regions of the gapmer-type ASO of the present invention are each independently 2 to 7 nucleotides long, preferably 3 to 5 nucleotides long, more preferably 3 nucleotides long. The length of the deoxy gap region of the gapmer-type ASO of the present invention is 7 to 10 nucleotides, preferably 8 to 10 nucleotides, more preferably 8 nucleotides. The full length of the gapmer-type ASO of the present invention is, for example, 12 to 25 nucleotides long, preferably 14 to 20 nucleotides long. Therefore, the gapmer-type ASO of the present invention can be appropriately adjusted by those skilled in the art under the conditions that satisfy all the specified ranges of the wing region length, the deoxy gap region length, and the full length.

More specifically, the gapmer-type ASO of the present invention is preferably, for example, a 14 nucleotide long "3-8-3" type gapmer, "3-9-2" type gapmer, "2-9-3" type gapmer, or "4-8-2" type gapmer; a 15 nucleotide long "3-9-3" type gapmer or "4-8-3" type gapmer; a 16 nucleotide long "5-8-3" type gapmer or "4-9-3" type gapmer; a 17 nucleotide long "5-8-4" type gapmer or "6-8-3" type gapmer; a 18 nucleotide long "6-8-4" type gapmer or "6-9-3" type gapmer; or a 20 nucleotide long "7-10-3" type gapmer.

In the gapmer-type ASO of the present invention, the sugar moiety of at least one nucleoside constituting the 5'- and 3'-wing regions is preferably modified by a bridge between the 2'-position and the 4'-position of the sugar. Examples of the bridge modification include modification with the aforementioned bridged nucleic acid. Preferred are LNA, AmNA, GuNA, and scpBNA. In a preferred embodiment of the gapmer-type ASO of the present invention, two or more (e.g., 2, 3, 4, 5) nucleotide residues constituting each of the 5' and 3' wing regions are replaced with bridged nucleic acids.

In a preferred embodiment, the DNA residue constituting the deoxy gap region of the gapmer-type ASO of the present invention is not sugar-modified.

In addition, the gapmer-type ASO of the present invention may be subjected to base modification in the deoxy gap region and dual modification in the wing region in order to reduce toxicity. Such modifications are described, for example, in WO 2018/155450.

Oligonucleotide Conjugate

The second invention described in this specification relates to an oligonucleotide conjugate having the antisense nucleic acid of the present invention.

This conjugate has a structure in which the antisense nucleic acid of the present invention and a molecule capable of binding to the asialoglycoprotein (ASGP) receptor are bound. The conjugate is described, for example, in WO 2018-216785, including the production methods.

In the oligonucleotide conjugate, one molecule containing a molecule capable of binding to an ASGP receptor (ASGP receptor-binding molecule) is bonded, or two or more of such molecules are bonded linearly to the 5'-end, 3'-end, or both ends of any of the antisense nucleic acids described above. ASGP receptors have the function of taking up in the liver and processing glycoprotein containing sugar chains with galactose or analogue thereof exposed at the end. Therefore, when two or more molecules containing an ASGP receptor-binding molecule are ligated, each molecule containing an ASGP receptor-binding molecule is desirably ligated in a manner allowing exposure of the ASGP receptor-binding molecule portion at the end (for example, an ASGP receptor-binding molecule binds to the side chain of a linker having a main chain and a side chain, and the main chains of the linkers are linearly linked and bind to the end(s) of the antisense nucleic acid, etc.). Therefore, "an ASGP receptor-binding molecule is bound to the end of the antisense nucleic acid" hereinafter means to encompass an embodiment in which a molecule containing an ASGP receptor-binding molecule binds via a portion other than the ASGP receptor-binding molecule.

The number of ASGP receptor-binding molecules may be 2 or more, or 3 or more, and may be 10 or less, 7 or less, or 5 or less. When ASGP receptor-binding molecule is bound to both ends of the antisense nucleic acid, the number of ASGP receptor-binding molecules is, for example, 4 or more and 20 or less.

Examples of the ASGP receptor binding molecule include asialoglycoproteins, more specifically lactose, galactose, N-acetylgalactosamine (GalNAc), galactosamine, N-formylgalactosamine, N-propionylgalactosamine, N-n-butanoylgalactosamine, N-iso-butanoylgalactosamine and derivatives thereof.

A preferred example of the ASGP receptor binding molecule is GalNAc. APOC3 protein is a protein expressed primarily in hepatocytes, and efficient antisense delivery to the liver permits still lower doses. As shown in the Examples, the activity of the antisense nucleic acid in the liver can be enhanced 10-fold or more by conjugating GalNAc to an antisense nucleic acid as a ligand for the ASGP receptor, which is a receptor specifically expressed in hepatocytes.

The ASGP receptor-binding molecule may be bound to the antisense nucleic acid via a known linker.

In an embodiment of the above-mentioned linker, for example, when two or more molecules capable of binding to ASGP receptor bind to an oligonucleotide, two or more main chain linkers are ligated and bound to the oligonucleotide, and a molecule capable of binding to an ASGP receptor is bound to each main chain linker via a side chain linker branched from the main chain. The main chain linker is not particularly limited, and a straight chain or branched chain, saturated or unsaturated carbon chain spacer can be recited as an example. Here, when the side chain linker contains a heteroatom as described later, the carbon chain may form a heterocyclic ring together with the carbon atoms of the main chain. The length of the carbon chain is not particularly limited. From the aspect of the degree of freedom of binding to the ASGP receptor of molecules capable of binding to the ASGP receptor, the lower limit of the carbon number is preferably 2 or more, and the upper limit is, for example, 18 or less, 16 or less, 12 or less, 10 or less, 8 or less, 6 or less, 5 or less, or 4 or less. Specifically, for example, ethylene chain, propylene chain, butylene chain, isopropylene chain, pentylene chain, hexylene chain, heptylene chain, octylene chain, nonylene chain, decylene chain, dodecylene chain, tetradecylene chain, hexadecylene chain, octadecylene chain, and the like can be mentioned. Two or more main chain linkers in a conjugate may be the same or different. Also, the side chain linker is not particularly limited, and examples thereof include linear or branched, saturated or unsaturated (optionally containing heteroatom and heterocycle) carbon chain spacers. The length of the carbon chain is not particularly limited, and about 5 to 50 carbon atoms are exemplified. These main chain linkers together with side chain linkers are sometimes simply referred to as a linker. The linker in the present invention preferably has a structure with a high degree of freedom from the aspect of promoting appropriate metabolism in cells. The linked molecules capable of binding to ASGP receptors preferably have a structure permitting flexible fitting into a spatially favorable arrangement of the ASGP receptors. Having such a linker structure, molecules capable of binding to ASGP receptors can be ligated individually with a degree of freedom. For example, when the main chain linker is a linear saturated carbon chain, the degree of freedom is higher than when it has a cyclic structure. Furthermore, the bond between a molecule capable of binding to an ASGP receptor and an oligonucleotide, that is, the bond between a linker and an oligonucleotide, is exemplified by a phosphodiester bond or a phosphorothioate bond. A phosphodiester bond is preferred since the oligonucleotide is appropriately metabolized in cells and efficiently acts on the target mRNA. One example in which molecules capable of binding to ASGP receptors are linked via a suitable linker is shown below.

Examples of specific conjugates are compound A1 and compound B1 below. These have three ASGP receptor-binding molecules bound to an antisense nucleic acid. In compound A1 and compound B1, three-dimensional wavy lines indicate antisense nucleic acids.

(compound A1)

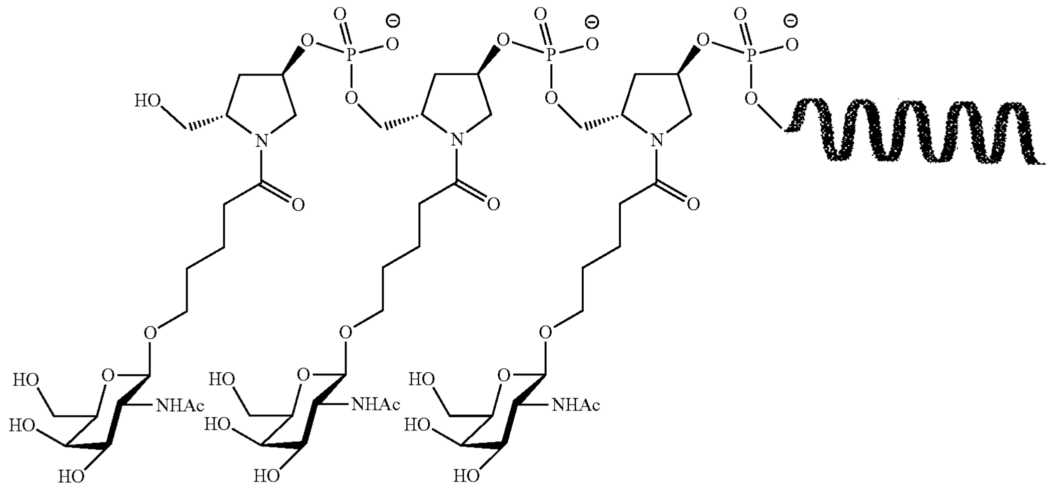

(compound B1)

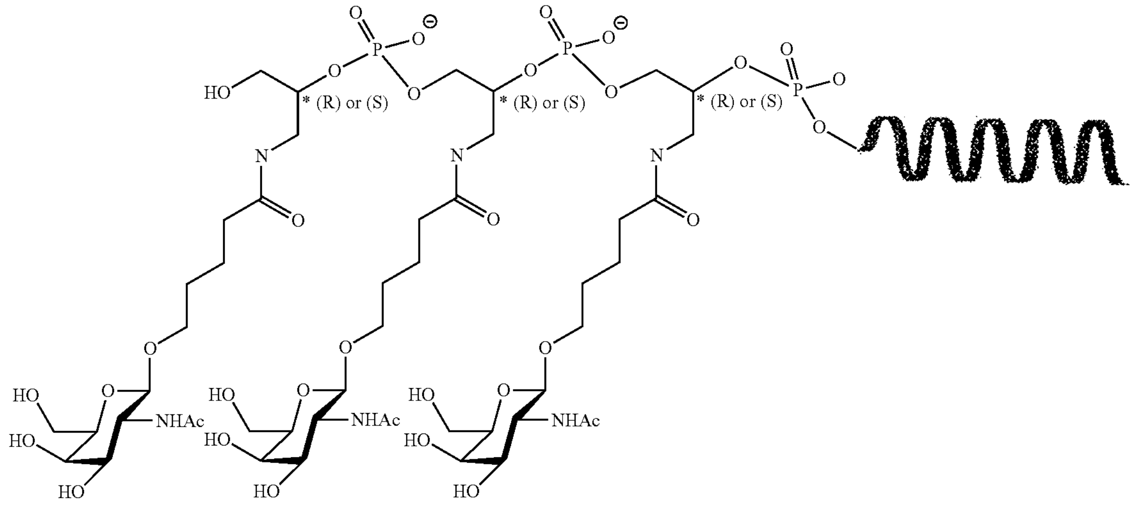

As explained above, the number of ASGP receptor-binding molecules is not limited to 3, and may be, for example, 1 or 2 or more and 10 or less. The formulas (A) and (B) of the conjugates represented by compound A1 and compound B1, respectively, are shown below.

(A)

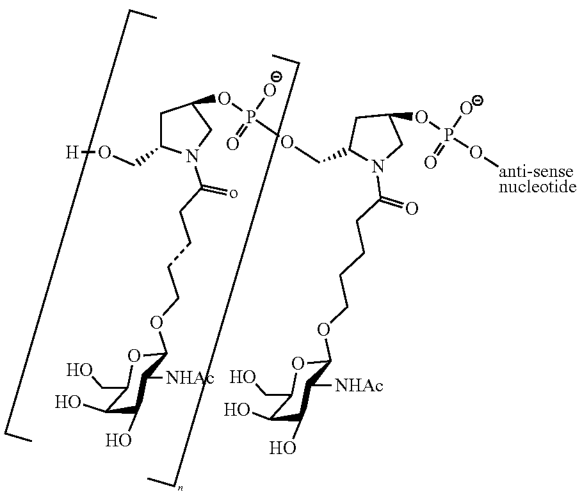

wherein n is an integer of 0 to 9.

(B)

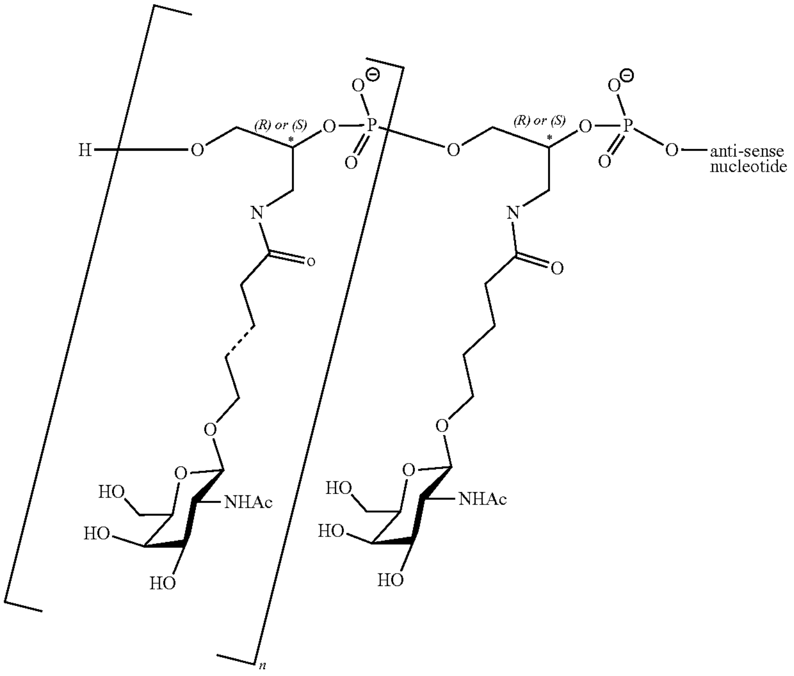

wherein n is an integer of 0 to 9.

For example, in formula (B), a compound having three (n=3) ASGP receptor-binding molecules (corresponding to compound B2 used in Examples 9 and 10) is also one example of a preferred conjugate. Substituents may be appropriately introduced into ASGP receptor-binding molecules having the structures of the formula (A) and the formula (B). In addition, the length of the alkylene portion of the linker portion may be changed as appropriate.

Pharmaceutical Composition and Medicament

The third invention described in this specification relates to a pharmaceutical composition or a medicament for inhibiting the expression of APOC3 protein, containing an effective amount of the antisense nucleic acid of the present invention as an active ingredient.

Examples of the medicament include therapeutic agents for hypertriglyceridemia and therapeutic agents for primary hyperchylomicronemia. The fourth invention described in this specification relates to a pharmaceutical composition or a medicament for inhibiting the expression of APOC3 protein, containing an effective amount of the above-mentioned oligonucleotide conjugate as an active ingredient. Examples of the medicament include therapeutic agents for hypertriglyceridemia and therapeutic agents for primary hyperchylomicronemia.

Hypertriglyceridemia is one of the hyperlipidemias in which the blood TG level is 150 mg/dL or more, and is recognized as a risk factor for coronary artery diseases. Apolipoproteins are involved in multifaceted roles in lipoprotein clearance, by inhibiting lipoprotein uptake into the liver, and inhibiting the enzyme lipoprotein lipase (LPL). It has been epidemiologically shown that individuals with decreased APOC3 function or loss-of-function type mutations in APOC3 have a 44% lower blood TG level and a 41% lower risk of coronary heart disease (Jorgensen, A. B., Frikke-Schmidt, R., Nordestgaard, B. G., and Tybjaerg-Hansen, A. (2014). Loss-of-function mutations in APOC3 and risk of ischemic vascular disease. N Engl J Med 371, 32-41.), and APOC3 is considered a good drug target of hypertriglyceridemia. Since the antisense nucleic acids and conjugates of the present invention inhibit APOC3 protein expression, they are effective as pharmaceutical compositions for inhibiting APOC3 protein expression and therapeutic agents for hypertriglyceridemia.

Hyperchylomicronemia is a disease in which chylomicrons accumulate in the blood. Chylomicron is produced in the small intestine and carries dietary nutrients (primarily "triglyceride" and certain vitamins) absorbed from the small intestine to systemic tissues. Triglyceride contained in chylomicron is degraded in the blood, and fatty acids, which are degradation products, are incorporated into systemic tissues. LPL enzyme degrades this triglyceride. When the action of LPL is prevented, chylomicrons accumulate, resulting in hyperchylomicronemia. As mentioned above, APOC3 protein inhibits the activity of the LPL enzyme. The antisense nucleic acid and the conjugates of the present invention inhibit the expression of APOC3 protein and are therefore effective as therapeutic agents for hyperchylomicronemia.

The pharmaceutical composition and the medicament contain an effective amount of the antisense nucleic acid or the oligonucleotide conjugate of the present invention as an active ingredient. These may contain the antisense nucleic acid or the oligonucleotide conjugate alone as an active ingredient, or may contain two or more kinds thereof as active ingredients. The pharmaceutical composition and the medicament may contain known pharmaceutically acceptable carriers in addition to the above-mentioned active ingredients. Examples of the pharmaceutically acceptable carrier include, but are not limited to, excipients such as sucrose, starch, and the like, binders such as cellulose, methylcellulose, and the like, disintegrants such as starch, carboxymethylcellulose, and the like, lubricants such as magnesium stearate, Aerosil, and the like, flavoring agents such as citric acid, menthol, and the like, preservatives such as sodium benzoate, sodium bisulfite, and the like, stabilizers such as citric acid, sodium citrate, and the like, suspending agents such as methylcellulose, polyvinyl pyrrolidone, and the like, dispersing agents such as surfactant and the like, diluents such as water, saline, and the like, base wax, and the like. The dosage form of the pharmaceutical composition or the medicament may be an oral administration preparation or a parenteral administration preparation (e.g., injection). In addition, the pharmaceutical composition and the medicament may be produced according to known methods.

The pharmaceutical composition and the medicament of the present invention can be orally or parenterally administered. Parenteral administration is desirable. A preparation preferred for parenteral administration (e.g., subcutaneous injection, intramuscular injection, topical injecting (e.g., intraventricular administration), intraperitoneal administration, and the like) is an aqueous or non-aqueous isotonic aseptic injection liquid which may contain antioxidant, buffer, bacteriostatic agent, isotonizing agent, and the like. In addition, an aqueous or non-aqueous aseptic suspension agent can be mentioned which may contain suspending agent, solubilizer, thickener, stabilizer, preservative, and the like. The preparation can be enclosed in a container in a unit dose or multiple doses like ampoules and vials. Alternatively, the active ingredient and a pharmaceutically acceptable carrier can also be lyophilized and stored in a state only requiring dissolving or suspending in a suitable sterile vehicle immediately before use.

The content of the antisense nucleic acid or oligonucleotide conjugate of the present invention in the pharmaceutical composition is, for example, about 0.1 to 100 wt % of the whole pharmaceutical composition.

The dose of the pharmaceutical composition or the medicament may be adjusted as appropriate, taking into consideration, for example, the age, gender, body weight, dosage form, and administration frequency of the subject of administration. Examples of the effective amounts are 0.01 μg to 1 g or 0.1 μg to 0.1 g of the antisense nucleic acid or the oligonucleotide conjugate of the present invention per administration per 50 kg body weight.

This specification also provides use of the antisense nucleic acid and the oligonucleotide conjugate of the present invention in the production of a pharmaceutical composition for inhibiting the expression of APOC3 protein, a therapeutic agent for hypertriglyceridemia, or a therapeutic agent for primary hyperchylomicronemia.

This specification also provides a method for inhibiting the expression of APOC3 protein in a subject (human), a method for treating hypertriglyceridemia, and a method for treating primary hyperchylomicronemia, including a step of administering the antisense nucleic acid or the oligonucleotide conjugate of the present invention to the subject.

Example 1

Synthesis of Antisense Nucleic Acid

An antisense oligonucleotide (or modified form thereof) was synthesized according to a conventional method.

An antisense nucleic acid can be synthesized using a known automatic nucleic acid synthesizer (e.g., manufactured by Applied Biosystems, DAINIPPON SEIKI Co., LTD., etc.). Examples of the method for synthesizing antisense nucleic acid include a solid phase synthesis process using phosphoramidite, and a solid phase synthesis process using hydrogen phosphonate, and are disclosed in, for example, Tetrahedron Letters 22, 1859-1862 (1981) and WO 2011/052436. Referring to the method described in Yamamoto, T., Sawamura, M., Wada, F., Harada-Shiba, M., and Obika, S. (2016). Serial incorporation of a monovalent GalNAc phosphoramidite unit into hepatocyte-targeting antisense oligonucleotides. Bioorg Med Chem 24, 26-32, modified nucleic acids No. 1 to No. 32 (Table 1) were synthesized.

TABLE 1

| ASO No. (SEQ ID NO:) | ASO sequence [1] | Position of target sequence [2] |
|---|---|---|
| No. 1 | GGGatgaactgAGc | 3-16 |
| No. 2 | GCTgcctctagGGa | 13-26 |
| No. 3 | GCAcctctgttCCt | 33-46 |
| No. 4 | AACaaggagtaCCc | 58-71 |
| No. 5 | GGAgggcaacaACa | 68-81 |
| No. 6 | AAGggaggcatCCt | 118-131 |
| No. 7 | TAAccctgcatGAa | 138-151 |
| No. 8 | GGGccacctggGAc | 203-216 |
| No. 9 | ACTgaagccatCGg | 238-251 |
| No. 10 | CTTtcagggaaCTg | 248-261 |
| No. 11 | CTCcagtagtcTTt | 258-271 |
| No. 12 | CTCagagaactTGt | 283-296 |
| No. 13 | CAGaactcagaGAa | 288-301 |
| No. 14 | TCAgggtccaaATc | 303-316 |

TABLE 1-continued

| ASO No. (SEQ ID NO:) | ASO sequence [1] | Position of target sequence [2] |
|---|---|---|
| No. 15 | TGAcctcagggTCc | 308-321 |
| No. 16 | TGGtctgacctCAg | 313-326 |
| No. 17 | GAAgttggtctGAc | 318-331 |
| No. 18 | CAGgcagccacGGc | 333-346 |
| No. 19 | GGTctcaggcaGCc | 338-351 |
| No. 20 | ATTgaggtctcAGg | 343-356 |
| No. 21 | GGGgtattgagGTc | 348-361 |
| No. 22 | TAGgcaggtggACt | 363-376 |
| No. 23 | ATGgataggcaGGt | 368-381 |
| No. 24 | TTGcaggacccAAg | 393-406 |
| No. 25 | TTAagcaacctACa | 423-436 |
| No. 26 | AGAatactgtcCCt | 438-451 |
| No. 27 | CACtgagaataCTg | 443-456 |
| No. 28 | GAGagcactgaGAa | 448-461 |
| No. 29 | GGAggccagcaTGc | 493-506 |
| No. 30 | TATtgggaggcCAg | 498-511 |
| No. 31 | AGCtttattggGAg | 503-516 |
| No. 32 | CTTcttgtccaGCt | 513-526 |

[1] upper-case letters: LNA (C is 5-methylcytosine LNA); lower-case letters: DNA; internucleoside bond is phosphorothioate bond

[2] nucleotide numbers of APOC3 mRNA (SEQ ID NO: 33) are indicated

Example 2

Screening for Antisense Nucleic Acid

A cell line derived from human liver cancer Huh-7 was plated onto a 96 well plate at 5000 cells/well, and cultured in DMEM (10% FBS, 1% penicillin, 1% streptomycin added) for 24 hr. Thereafter, the culture medium was replaced with $Ca^{2+}$ enriched medium (CEM: DMEM with 10% FBS, 9 mM $CaCl_2$) supplemented with each antisense having 2',4'-bridged sugar moiety (LNA) at a final concentration of 200 nM, and the cells were further cultured for 24 hr. Thereafter, using SuperPrep (registered trade mark) II Cell Lysis & RT Kit for qPCR (TOYOBO), cDNA was prepared from the cell lysate, and GAPDH mRNA and APOC3 mRNA were quantified with the StepOnePlus™ real-time PCR system (Applied Biosystems) using the following probes. The expression level of APOC3 normalized with GAPDH was calculated as a relative value with the antisense non-treatment (NT:non-treat) as 1. The results thereof are shown in FIG. 1.

Human GAPDH mRNA: hs02786624_g1

Human APOC3 mRNA: hs00906501_g1

Example 3

Screening for Antisense Nucleic Acid

Figure 2:
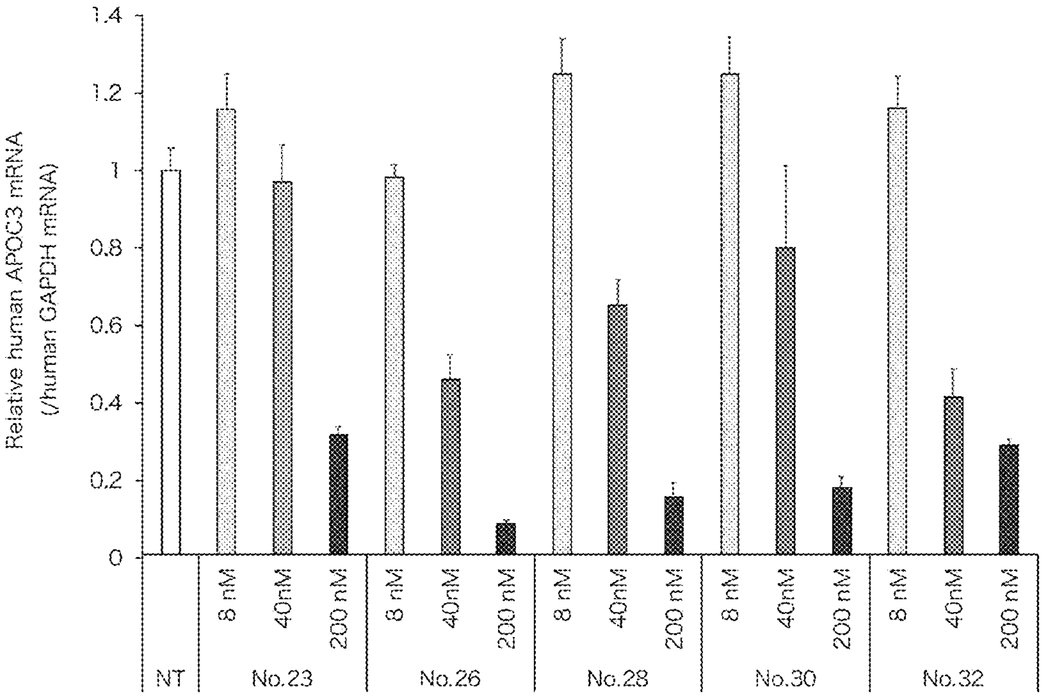
FIG. 2 shows the results of the second in vitro screening for antisense nucleic acids targeting human APOC3 mRNA using CEM method.

Five types of antisense nucleic acids (No. 23, No. 26, No. 28, No. 30, No. 32) targeting 3'UTR that showed high APOC3 expression inhibitory activity in Example 2 were examined for concentration dependency of the inhibition of APOC3 gene expression, by replacing the 2',4'-bridged nucleic acid in sugar moiety with AmNA. A cell line derived from human liver cancer Huh-7 was plated onto a 96 well plate at 5000 cells/well, and cultured in DMEM (10% FBS, 1% penicillin, 1% streptomycin added) for 24 hr. Thereafter, the culture medium was replaced with $Ca^{2+}$ enriched medium (CEM: DMEM with 10% FBS, 9 mM $CaCl_2$) supplemented with each antisense having AmNA modification at a final concentration of 8, 40, or 200 nM, and the cells were further cultured for 24 hr. Thereafter, using SuperPrep (registered trade mark) II Cell Lysis & RT Kit for qPCR (TOYOBO), cDNA was prepared from the cell lysate, GAPDH mRNA and APOC3 mRNA were quantified with the StepOnePlus™ real-time PCR system (Applied Biosystems) using the following probes. The expression level of APOC3 normalized with GAPDH was calculated as a relative value with the antisense non-treatment (NT: non-treat) as 1. The results thereof are shown in FIG. 2. All antisense nucleic acids inhibited APOC3 expression in a concentration dependent manner.

Human GAPDH mRNA: hs02786624_g1

Human APOC3 mRNA: hs00906501_g1

Example 4

Comparison with Known Drug

A cell line derived from human liver cancer Huh-7 was plated onto a 96 well plate at 5000 cells/well, and cultured in DMEM (10% FBS, 1% penicillin, 1% streptomycin added) for 24 hr. Thereafter, the culture medium was replaced with $Ca^{2+}$ enriched medium (CEM: DMEM with 10% FBS, 9 mM $CaCl_2$) supplemented with a modified antisense nucleic acid (antisense nucleic acid No. 26 (LNA modified)) having the base sequence depicted in SEQ ID NO: 26 at a final concentration of 100 nM or 200 nM, and the cells were further cultured for 24 hr.

Using SuperPrep (registered trade mark) II Cell Lysis & RT Kit for qPCR (TOYOBO), cDNA was prepared from the cell lysate, GAPDH mRNA and APOC3 mRNA were quantified with the StepOnePlus™ real-time PCR system (Applied Biosystems) using the following probes, and the expression level of APOC3 normalized with GAPDH was calculated.

Human GAPDH mRNA: hs02786624_g1 (Applied Biosystems)

Human APOC3 mRNA: hs00906501_g1 (Applied Biosystems)

The base sequence of antisense nucleic acid No. 26 (LNA modified) was as shown below.

AGAatactgtcCCt (SEQ ID NO: 26)

(upper-case letters show LNA, and lower-case letters show DNA)

Comparative Example 1

In the same manner as in Example 4 except that an oligonucleotide (Gene Co., Ltd.) with the same sequence and the same modification (central 10 nucleotides are DNA, 5 nucleotides at each end are 2'MOE modified, all internucleotide bonds are phosphorothioate bonds) as volanesorsen (antisense nucleic acid complementary to the base sequence shown at positions 3533-3552 of SEQ ID NO: 4 (base sequence of primary transcript of APOC3) of Patent Literature 2) was used instead of antisense nucleic acid No. 26 (LNA modified), GAPDH mRNA and APOC3 mRNA were quantified and the expression level of APOC3 normalized with GAPDH was calculated.

Figure 3:
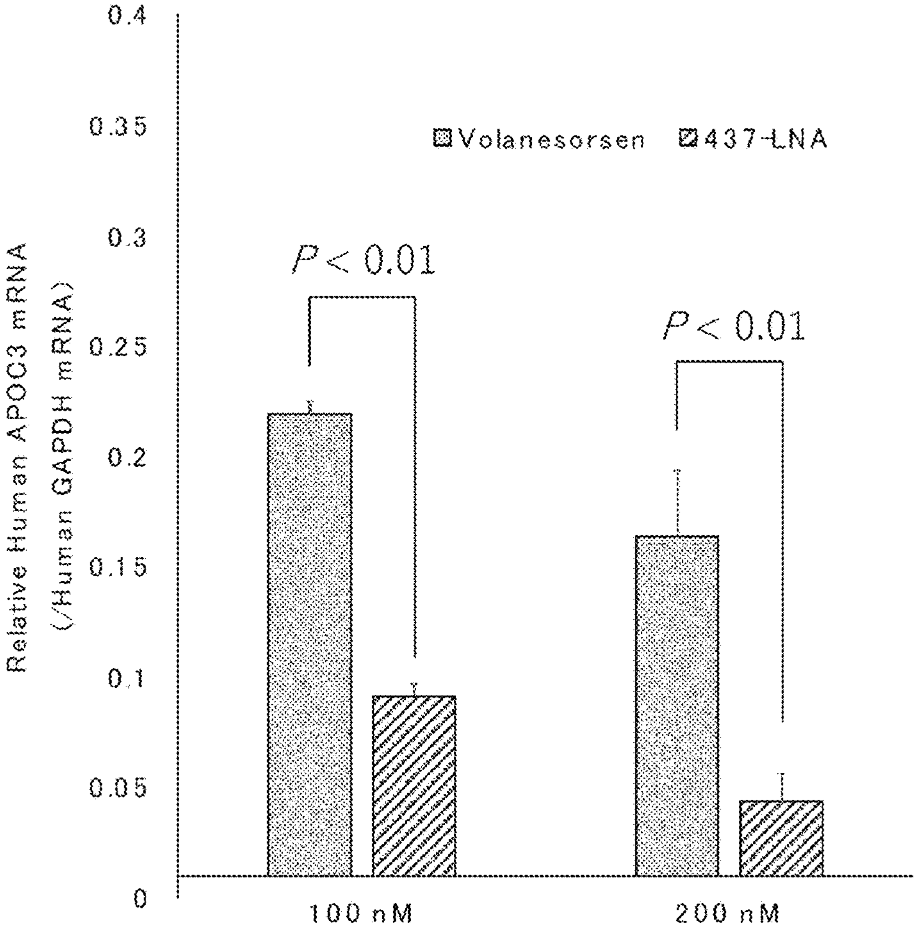
FIG. 3 shows comparison between a known drug for Huh-7 (Comparative Example) and antisense nucleic acid No. 26 in suppressive effect on human APOC3 mRNA expression.

The measurement results of Example 4 and Comparative Example 1 were expressed as relative values with the antisense non-treatment as 1, and compared. P value was calculated by student's t-test. The results thereof are shown in FIG. 3. As shown in FIG. 3, antisense nucleic acid No. 26 showed significantly higher gene expression suppressive activity than the antisense nucleic acid of Comparative Example 1. It was shown that the antisense nucleic acid with a bridged sugar moiety and having the nucleotide sequence depicted in SEQ ID NO: 26 has higher activity than conventional medicaments, and thus exhibits, even at a lower dose, higher efficacy than the conventional medicaments.

Example 5

Figure 4:
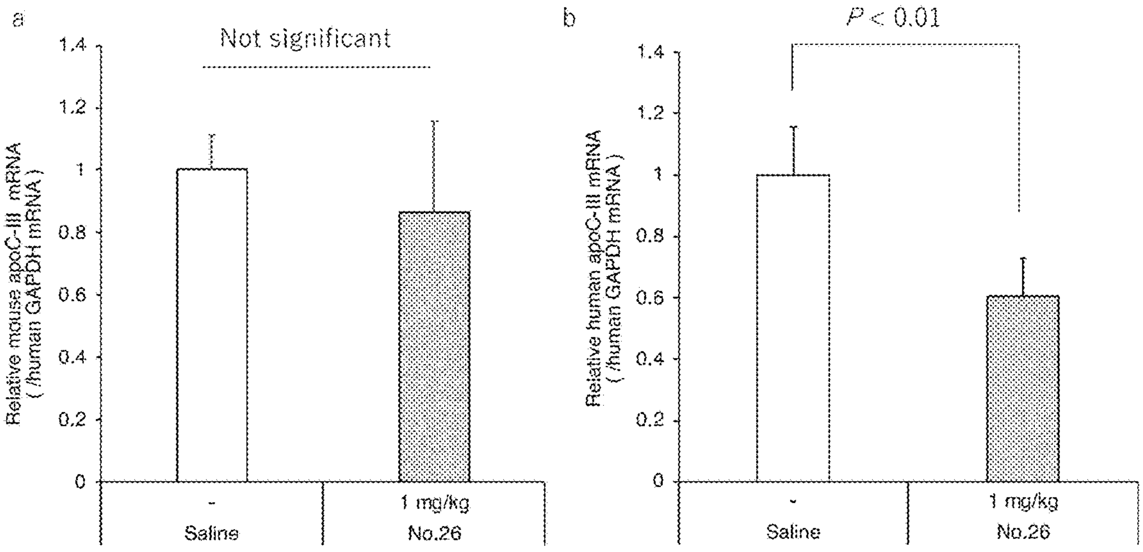
FIG. 4 shows the selective suppressive effect of a GalNAc conjugate of antisense nucleic acid No. 26 on human APOC3 mRNA expression in human liver chimeric mice.

In order to predict effectiveness in humans, antisense nucleic acid No. 26 (LNA modified) conjugated with GalNAc having the structure of the aforementioned compound A was subcutaneously administered once at a dose of 1 mg/kg to human liver chimeric mice (PhoenixBio Co., LTD.) in which hepatocytes were replaced with human hepatocytes. Seven days after the administration, blood was collected and an autopsy of the liver was performed, and serum ALT levels and human APOC3 mRNA and human GAPDH mRNA in the liver were quantified. Human APOC3 mRNA was detected by StepOnePlusm real-time PCR system (Applied Biosystems) using the following Taqman probes, and human GAPDH mRNA was detected by SYBR Green using the following primers. P value was calculated by student's t-test. The results thereof are shown in FIG. 4.

Human APOC3 mRNA: hs00906501_g1 (Applied Biosystems)

Human GAPDH mRNA:

```
Fw
                              (SEQ ID NO: 35)
5'GCACCGTCAAGGCTGAGAAC3'

Rv
                              (SEQ ID NO: 36)
5'TGGTGAAGACGCCAGTGGA3'

                              (SEQ ID NO: 26)
XXXA^G^A^a^t^a^c^t^g^t^c^c^c^t
```

X shows N-acetylgalactosamine (GalNAc)-containing monomer molecule of compound A1, upper-case letters show LNA (Locked Nucleic Acid) (C is 5-methylcytosine LNA), lower-case letters show DNA, and Internucleoside bond ^ shows a phosphorothioate bond.

As shown in FIG. 4a, no effect was observed on mouse apoc3 mRNA in mouse liver remaining in the mouse and, as shown in FIG. 4b, a specific expression suppressive effect was found on human apoc3 mRNA in human hepatocytes.

Example 6

Effectiveness Confirmation Test in *Macaca fascicularis*

In order to predict effectiveness in humans, antisense nucleic acid No. 26 (LNA modified) conjugated with GalNAc having the structure of the aforementioned compound A1 was subcutaneously administered once at a dose of 3 mg/kg to two *Macaca fascicularis* (4 years old, male) that are animals with comparatively high gene homology to apoC3. Two days before administration, three days after administration, and seven days after administration, the blood was collected from the femoral vein and centrifuged at 1,700×g for 10 min to obtain serum. Using the serum, serum triglyceride concentration was measured with JCA-BM6070 (JEOL Ltd.).

Figure 5:
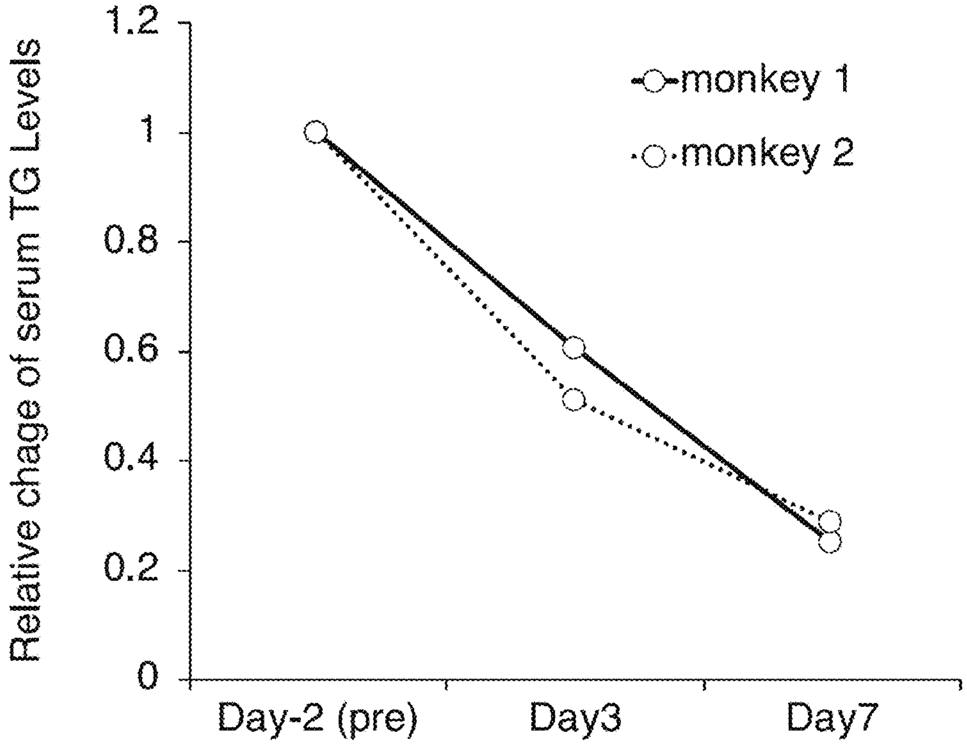
FIG. 5 shows the effect of a GalNAc conjugate of antisense nucleic acid No. 26 on blood triglyceride reduction in *Macaca fasciculari*.

As a result, a remarkable decrease in the serum triglyceride level was observed in the both *Macaca fascicularis* (FIG. 5).

Example 7

In Vitro Activity of 14-20 Mer Antisense Nucleic Acid Similar to Antisense Nucleic Acid No. 26

In the same manner as in Example 1, antisense nucleic acid No. 26-2 (SEQ ID NO: 37) to antisense nucleic acid No. 26-6 (SEQ ID NO: 41) that are 14-20 mer antisense nucleic acids similar to antisense nucleic acid No. 26 were synthesized.

```
No. 26-2:
                              (SEQ ID NO: 37)
TgAgAatactgtcCCt

No. 26-3:
                              (SEQ ID NO: 38)
GAgAatactgtcCCt

No. 26:
                              (SEQ ID NO: 26)
AGAatactgtcCCt

No. 26-4:
                              (SEQ ID NO: 39)
AGAatactgtccCTt

No. 26-5:
                              (SEQ ID NO: 40)
TgAgAatactgtccCTt

No. 26-6:
                              (SEQ ID NO: 41)
AcTgagAatactgtcccTtT
```

upper-case letters show LNA (Locked Nucleic Acid) (C is 5-methylcytosine LNA), lower-case letters show DNA, upper-case letters+underline shows 2'-O-Me modification, and internucleoside bond shows a phosphorothioate bond.

Figure 6:
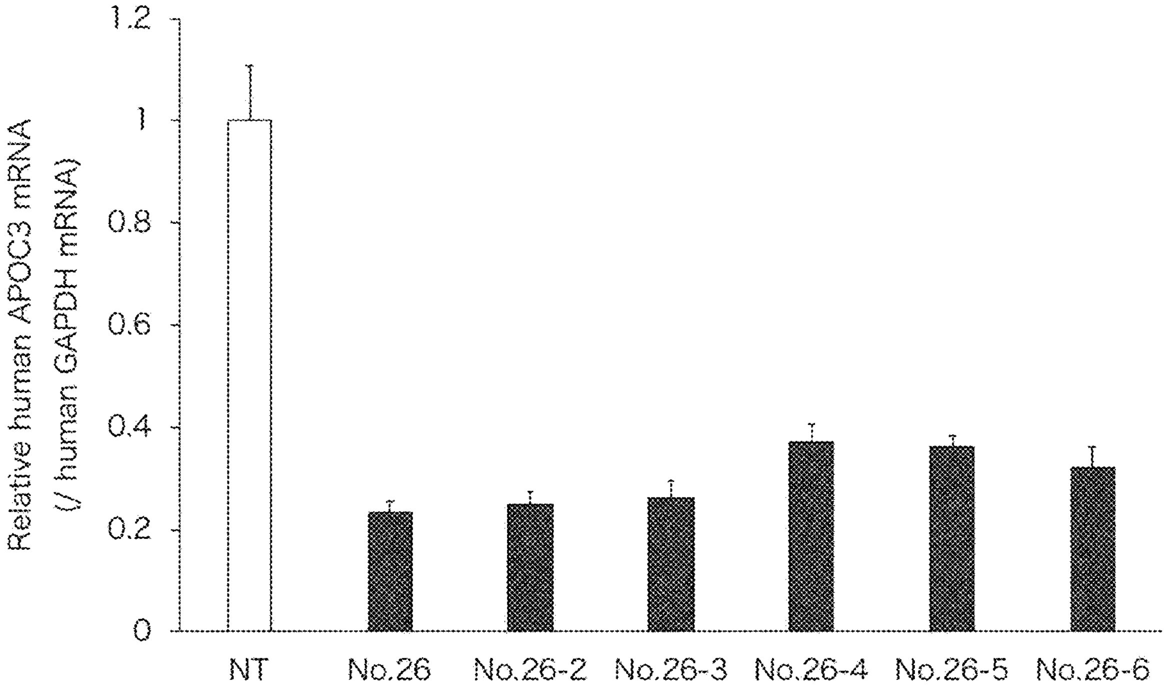
FIG. 6 shows the results of evaluation of in vitro activity of antisense nucleic acids targeting human APOC3 mRNA.

In the same manner as in Example 2, APOC3 expression inhibitory activity of antisense nucleic acid No. 26 and Nos. 26-2 to No. 26-6 was measured. As a result, all antisense nucleic acid No. 26 derivatives (No. 26-2 to No. 26-6) showed high APOC3 expression inhibitory activity similar to that of antisense nucleic acid No. 26 (FIG. 6).

Example 8

In order to predict effectiveness in humans, antisense nucleic acid No. 26 (LNA modified) conjugated with GalNAc having the structure of compound B1 was subcutaneously administered once at a dose of 1 mg/kg to two *Macaca fascicularis* (2-5 years old, male) that are animals with comparatively high gene homology to apoC3. Seven days after the administration, an autopsy of the liver was performed, and APOC3 mRNA and GAPDH mRNA in the liver were quantified. APOC3 mRNA and GAPDH mRNA were detected by StepOnePlus™ real-time PCR system (Applied Biosystems) using the following Taqman probes. The relative value was calculated with the value in *Macaca fascicularis* without administration of the antisense nucleic acid No. 26 as 1.

*Macaca fascicularis* GAPDH mRNA: Mf04392546_g1

*Macaca fascicularis* APOC3 mRNA: Mf02794312_m1

Figure 7:
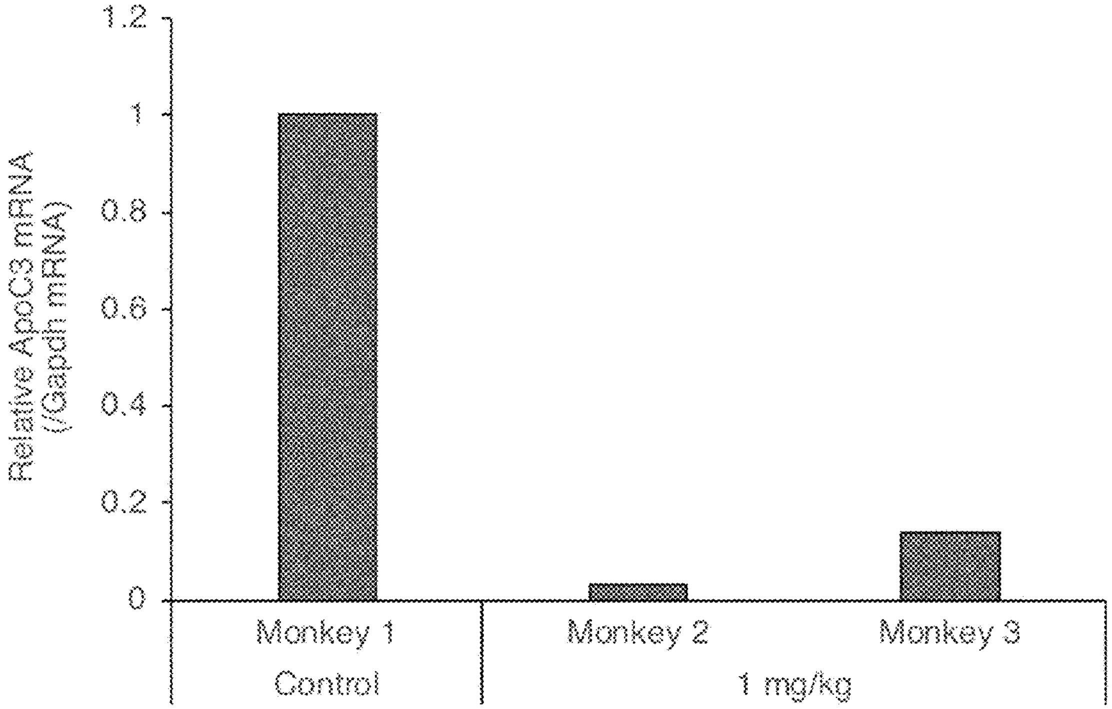
FIG. 7 shows the effect of a GalNAc conjugate of antisense nucleic acid No. 26 on blood triglyceride reduction in *Macaca fasciculari*.

The results thereof are shown in FIG. 7.

As shown in FIG. 7, a decrease of 85% or more in APOC3 mRNA was confirmed in the both *Macaca fascicularis.*

Example 9

In order to confirm the effectiveness of No. 26 (SEQ ID NO: 26) conjugated with 4 molecules of GalNAc like compound B2, subcutaneous administration was performed once to 12 *Macaca fascicularis* (3-5 years old, male) at a dose of 3 mg/kg.

(compound B2)

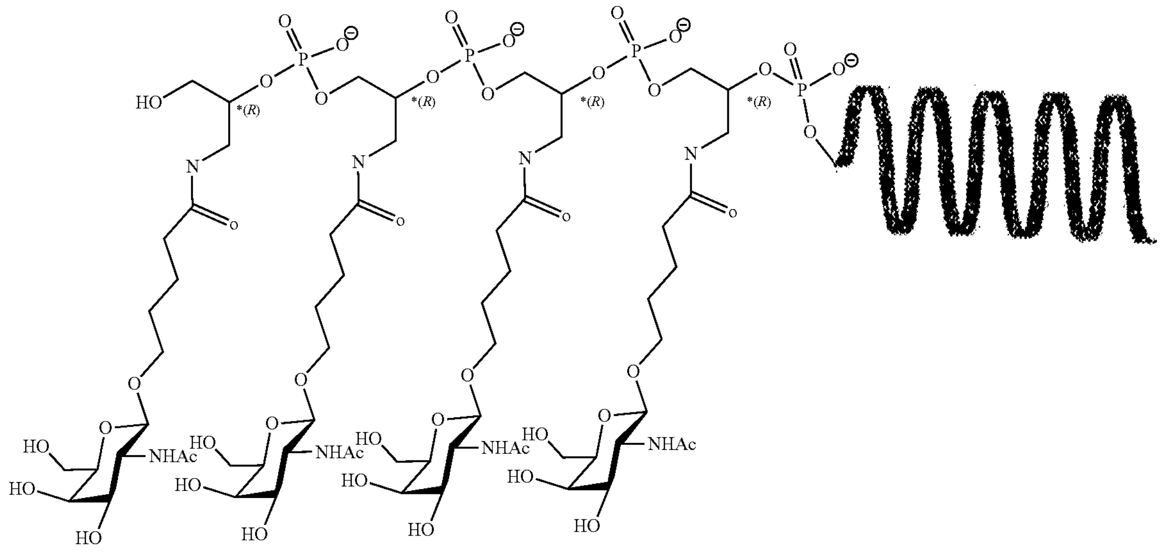

wherein three-dimensional wavy line shows antisense nucleic acid.

At 3 (Group 1), 28 (Group 2), 56 (Group 3), and 91 days (Group 4) after administration, blood collection and an autopsy of the liver were performed on 3 animals each. The collected blood was centrifuged (room temperature, 1700×g, 10 min) to obtain serum, and the concentration of ALT and creatinine was measured using an automatic analyzer (JCA-BM6070, JEOL Ltd.). In addition, the autopsied liver was immersed in RNAlater (Thermo Fisher Scientific), stored overnight in a refrigerator, and then transferred to an ultra-low temperature freezer (−70° C.) and stored. cDNA was prepared from total RNA extracted from the liver, and APOC3 mRNA and GAPDH mRNA in the liver were quantified. APOC3 mRNA and GAPDH mRNA were detected by StepOnePlus™ real-time PCR system (Applied Biosystems) using the following Taqman probes. The relative value was calculated with the value in *Macaca fascicularis* without administration of the antisense as 1.

*Macaca fascicularis* GAPDH mRNA: Mf04392546_g1

*Macaca fascicularis* APOC3 mRNA: Mf02794312_m1

Figure 8:
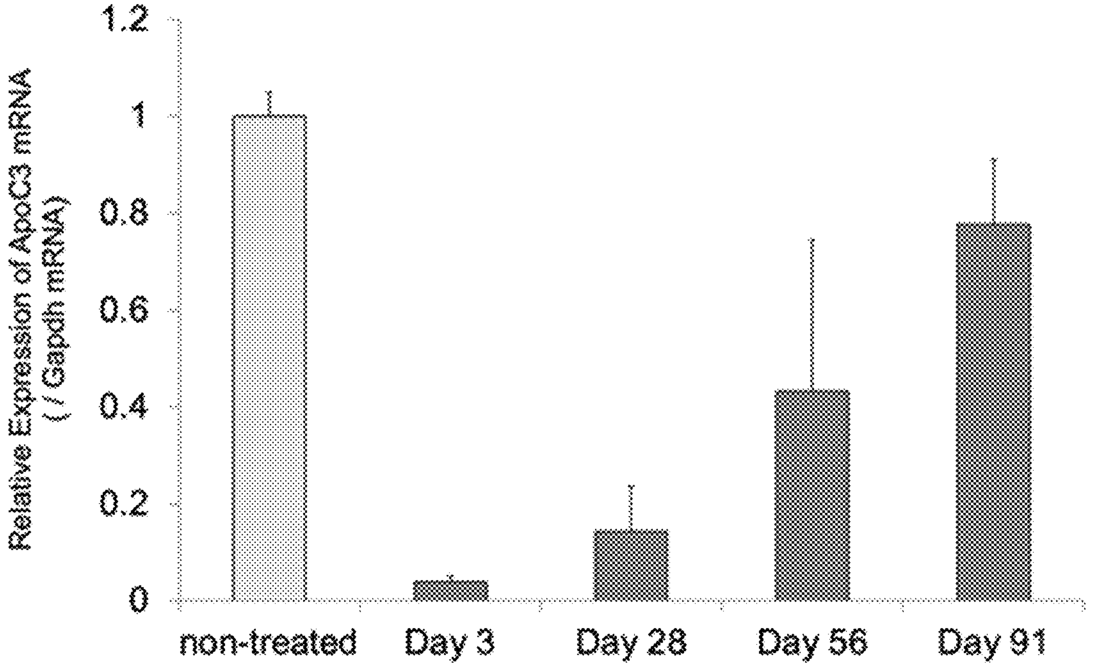
FIG. 8 shows the suppressive effect of a GalNAc conjugate of antisense nucleic acid No. 26 on APOC3 mRNA expression in *Macaca fasciculari*.
Figure 9:
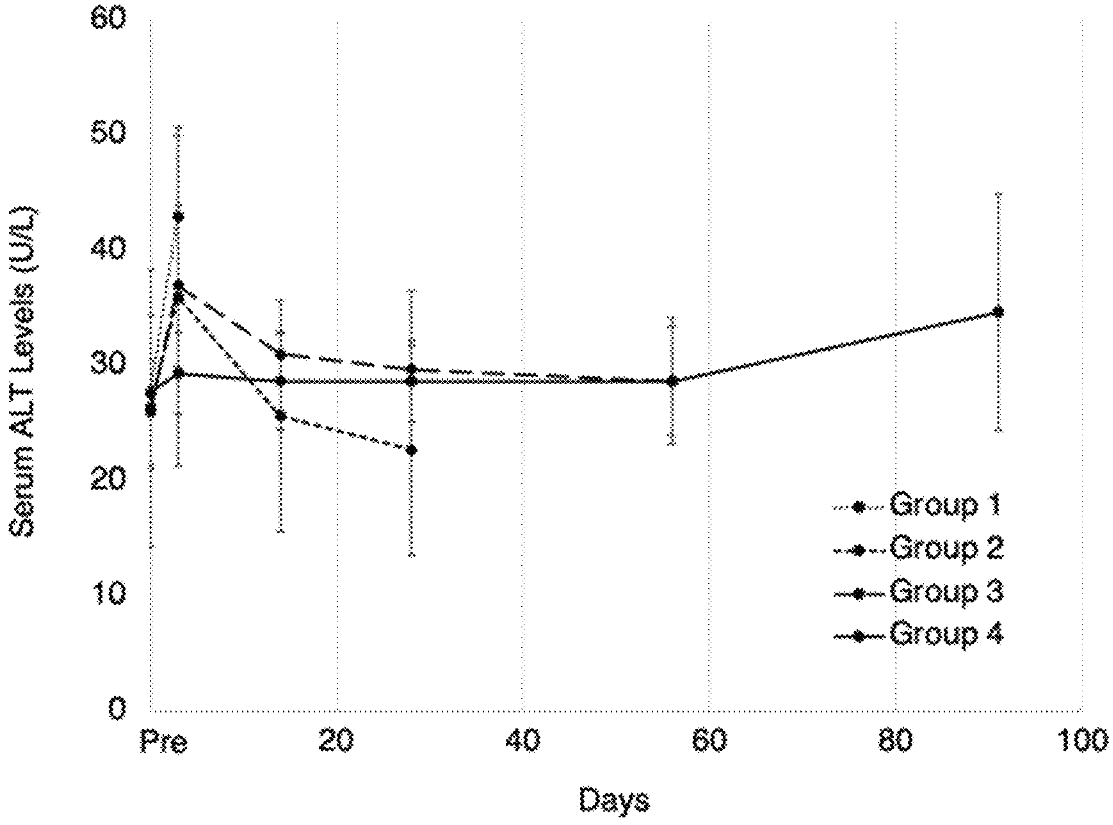
FIG. 9 shows the serum ALT value profile in *Macaca fasciculari* administered with a GalNAc conjugate of antisense nucleic acid No. 26.
Figure 10:
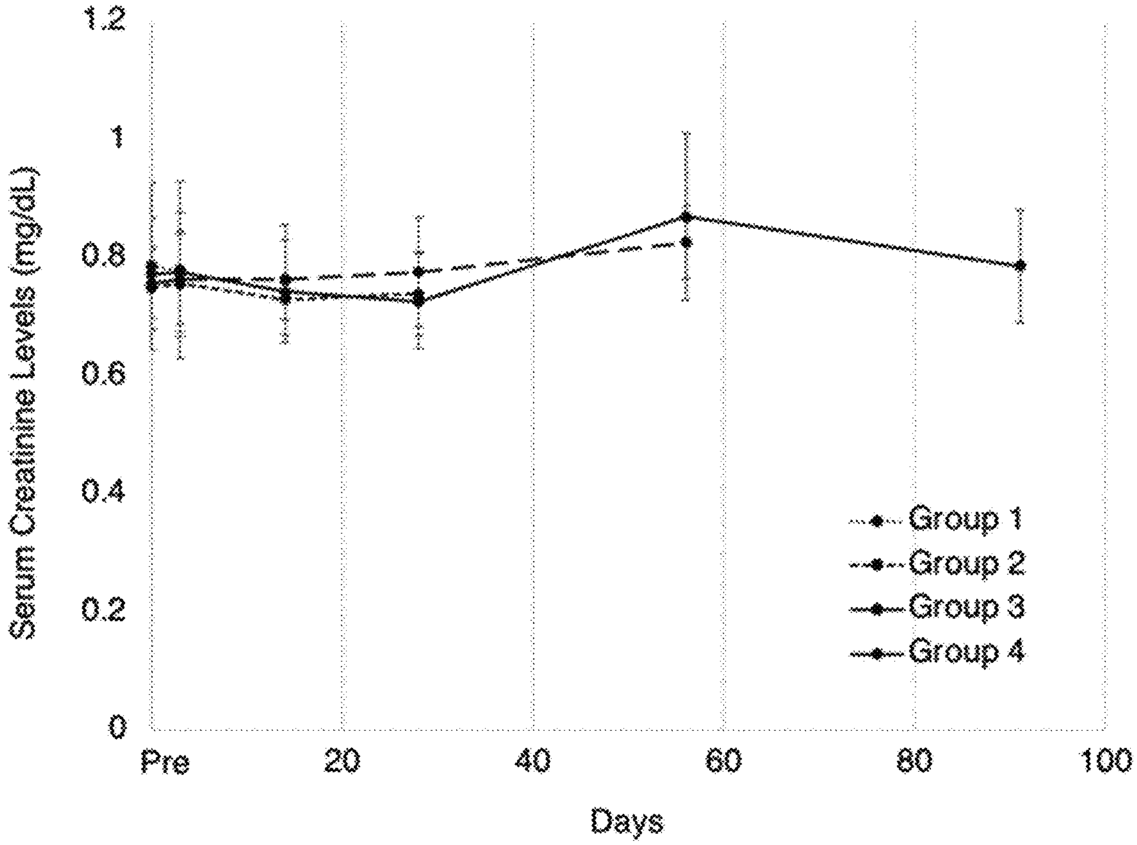
FIG. 10 shows the serum creatinine value profile in *Macaca fasciculari* administered with a GalNAc conjugate of antisense nucleic acid No. 26.

As a result, as shown in FIG. 8, APOC3 mRNA in the liver decreased significantly over 56 days after administration. As shown in FIGS. 9 and 10, although a temporary increase in the serum ALT level was observed, the serum ALT level and creatinine level remained almost normal for 91 days or more after administration.

Example 10

In order to confirm the safety of No. 26 (SEQ ID NO: 26) conjugated with 4 molecules of GalNAc as in compound B2, subcutaneous administration was performed once to *Macaca fascicularis* (2-4 years old, male) at a dose of 0.5, 1, 3, 20 mg/kg, 3 animals for each dose. As a comparison target, saline was administered to 3 animals. At 4, 7, 14, 21, 28, 35, 42, 49, 56, 63, 70, 77, 84, and 90 days after the administration, the blood was collected once. The collected blood was centrifuged (room temperature, 1700×g, 10 min) to obtain serum, and the concentration of ALT and creatinine was measured using an automatic analyzer (JCA-BM6070, JEOL Ltd.).

Figure 11:
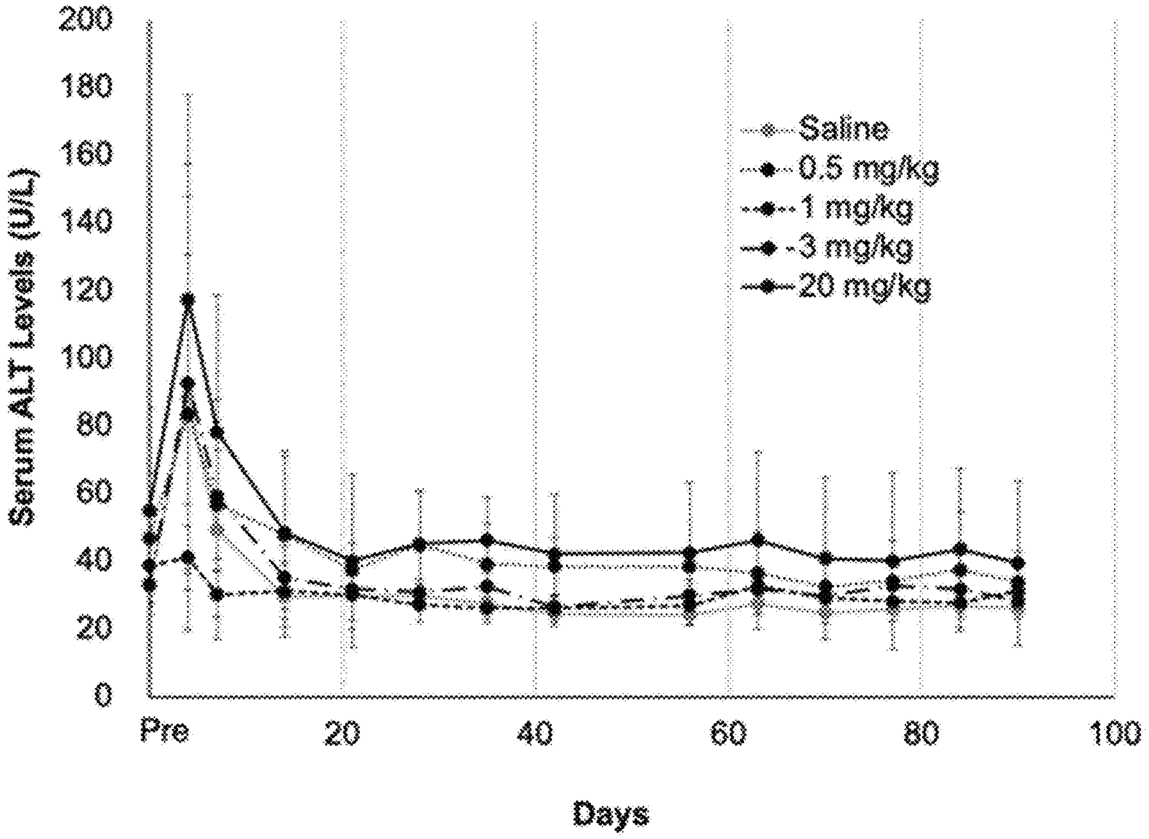
FIG. 11 shows the serum ALT value profile in *Macaca fasciculari* administered with various doses of a GalNAc conjugate of antisense nucleic acid No. 26.
Figure 12:
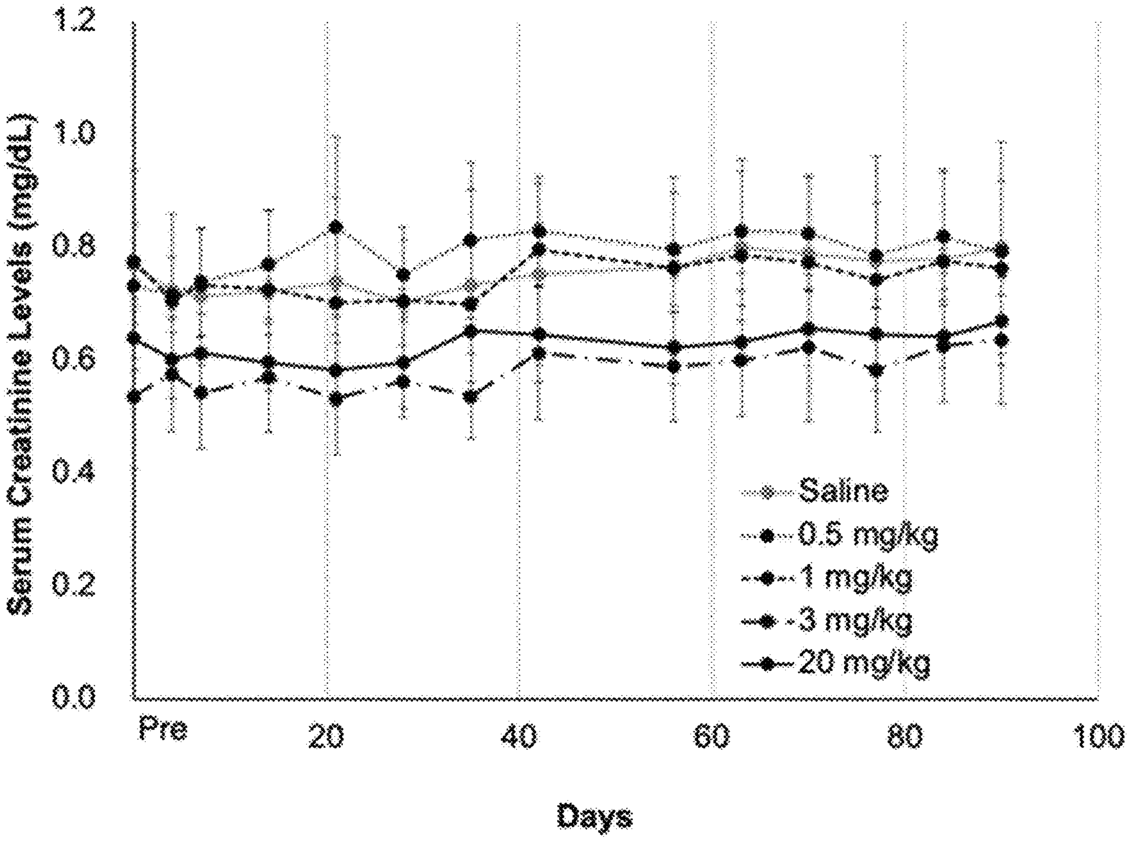
FIG. 12 shows the serum creatinine value profile in *Macaca fasciculari* administered with various doses of a GalNAc conjugate of antisense nucleic acid No. 26.

As a result, although a temporary increase in the ALT level was confirmed, dose dependency was not confirmed (FIG. 11). Since similar changes were also observed in the Saline administration group, it is considered that the changes were not derived from the test substance. Moreover, no change was found in the creatinine value (FIG. 12).

Example 11

In Vitro Activity of Antisense Nucleic Acid No. 26-3 (SEQ ID NO: 38) Analogs

No. 26-7 to No. 26-13 which are analogs of antisense nucleic acid No. 26-3 (SEQ ID NO: 38) were synthesized. In the same manner as in Example 1, in vitro activity was measured at a concentration of 50 nM, compared with antisense nucleic acid No. 26 (SEQ ID NO: 26), and evaluated.

No. 26-3: (SEQ ID NO: 38)

GAgAatactgtcCCt

-continued

No. 26-7:

(SEQ ID NO: 38)

GAG$^{R}\underline{\text{A}}$atactgtcCCt

No. 26-8:

(SEQ ID NO: 38)

GAG$^{F}\underline{\text{A}}$atactgtcCCt

No. 26-9:

(SEQ ID NO: 38)

GA$\underline{\text{GA}}$atactgtcCCt

No. 26-10:

(SEQ ID NO: 38)

GAG$^{F}$A$^{R}$atactgtcCCt

No. 26-11:

(SEQ ID NO: 38)

GA$^{R}$G$\underline{\text{A}}$atactgtcCCt

No. 26-12:

(SEQ ID NO: 38)

GA$^{F}$G$\underline{\text{A}}$atactgtcCCt

No. 26-13:

(SEQ ID NO: 38)

G$\underline{\text{A}}$G$\underline{\text{A}}$atactgtcCCt upper-case letters show LNA (Locked Nucleic Acid) (C is 5-methylcytosine LNA), lower-case letters show DNA, upper-case letters+underline shows 2'-O-Me modification, N$^{R}$ shows RNA(2'-OH) ("N" is any base, hereinafter the same), N$^{F}$ shows 2'-Fluoro modification, and each internucleoside bond shows a phosphorothioate bond.

Figure 13:
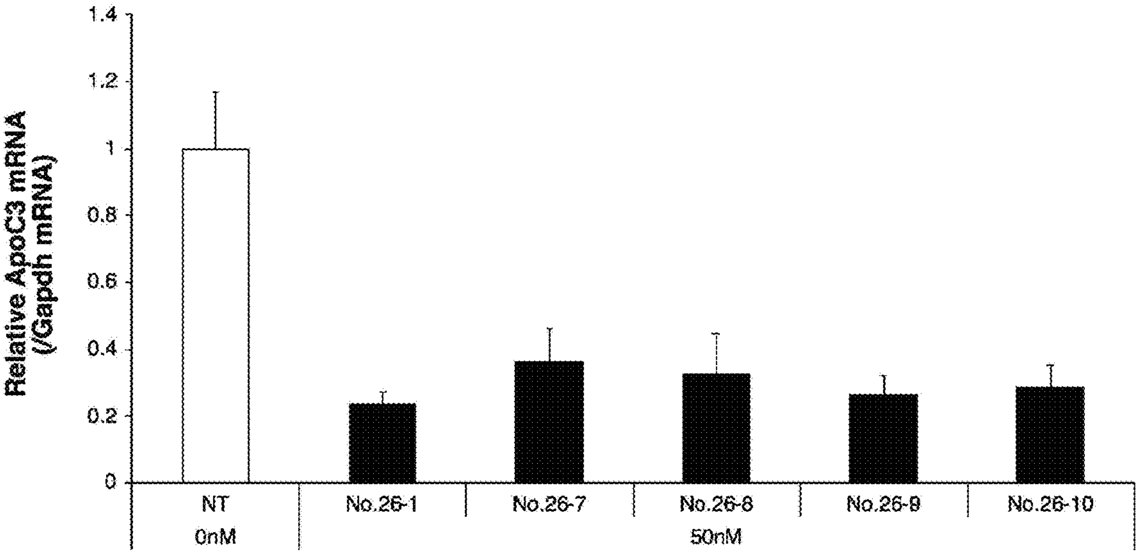
FIG. 13 shows the in vitro suppressing activity of antisense nucleic acid No. 26-3 (SEQ ID NO: 38) analogs against APOC3 mRNA expression.
Figure 13:
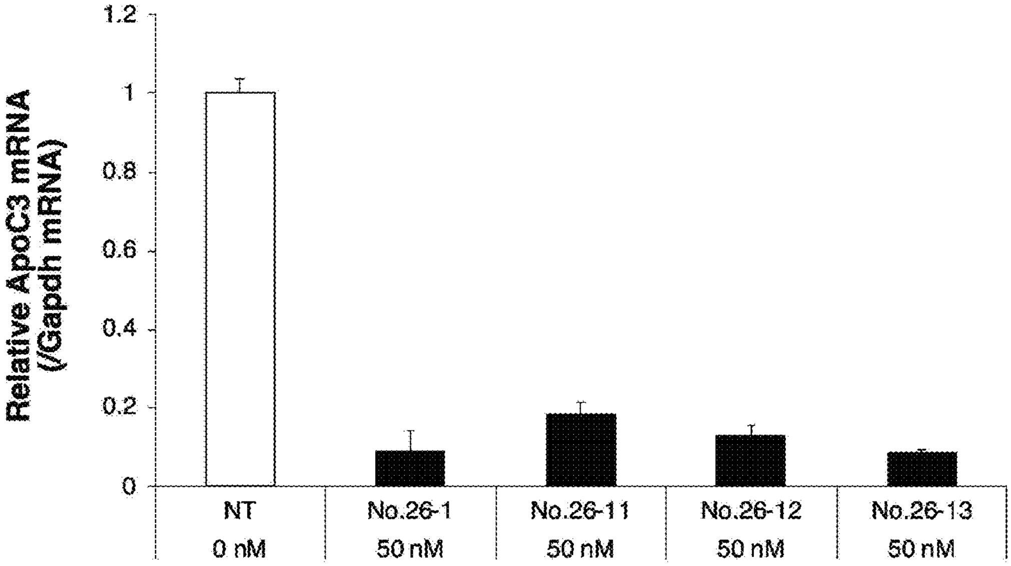

As a result, all antisense nucleic acid No. 26-3 analogs (No. 26-7 to No. 26-13) showed high APOC3 expression inhibitory activity similar to that of antisense nucleic acid No. 26 (FIG. 13).

From the above-mentioned Examples, it has been shown that the antisense nucleic acid depicted in SEQ ID NO: 26 and having bridged sugar moiety, various derivatives thereof, and conjugates thereof have remarkable effects compared with conventional drugs, inhibit APOC3 protein expression, and are effective as active ingredients of therapeutic agents for hypertriglyceridemia and therapeutic agents for primary hyperchylomicronemia.

INDUSTRIAL APPLICABILITY

This invention can be used in the pharmaceutical industry.

This application is based on a patent application No. 2020-55717 filed in Japan (filing date: Mar. 26, 2020), the contents of which are incorporated in full herein by reference.

The invention claimed is:

1. An antisense oligomer, pharmaceutically acceptable salt thereof or pharmaceutically acceptable hydrate thereof consisting of any of the following base sequences:

(SEQ ID NO: 26)
AGAatactgtcCCt (SEQ ID NO: 37)
$\mathrm{TgAg\underline{A}atactgtcCCt}$ (SEQ ID NO: 38)
$\mathrm{GAg\underline{A}atactgtcCCt}$ (SEQ ID NO: 39)
$\mathrm{AG\underline{A}atactgtccCTt}$ (SEQ ID NO: 40)
$\mathrm{TgAg\underline{A}atactgtccCTt}$ (SEQ ID NO: 41)
$\mathrm{AcTgag\underline{A}atactgtcccTtT}$ (SEQ ID NO: 38)
$\mathrm{GAG^{R}\underline{A}atactgtcCCt}$ (SEQ ID NO: 38)
$\mathrm{GAG^{F}\underline{A}atactgtcCCt}$ (SEQ ID NO: 38)
$\mathrm{GA\underline{GA}atactgtcCCt}$ (SEQ ID NO: 38)
$\mathrm{GAG^{F}A^{R}atactgtcCCt}$ (SEQ ID NO: 38)
$\mathrm{GA^{R}G\underline{A}atactgtcCCt}$ (SEQ ID NO: 38)
$\mathrm{GA^{F}G\underline{A}atactgtcCCt}$ (SEQ ID NO: 38)
$\mathrm{G\underline{A}G\underline{A}atactgtcCCt}$ wherein upper-case letters indicate LNA (Locked Nucleic Acid) (C is 5-methylcytosine LNA), lower case letters indicate DNA, upper case letters+underline indicates 2'-O-Me modification, $N^R$ indicates RNA (2'-OH) ("N" indicates any base), $N^F$ indicates 2'-Fluoro modification, and each internucleoside bond indicates phosphorothioate bond.

2. An oligonucleotide conjugate wherein a molecule capable of binding to an asialoglycoprotein receptor is added to one or both ends of the oligonucleotide strand of the antisense oligomer, pharmaceutically acceptable salt thereof or pharmaceutically acceptable hydrate thereof according to claim 1, wherein the molecule capable of binding to an asialoglycoprotein receptor is selected from the group consisting of lactose, galactose, N-acetylgalactosamine (GalNAc), galactosamine, N-formylgalactosamine, N-propionylgalactosamine, N-n-butanoylgalactosamine, and N-isobutanoylgalactosamine.

3. The oligonucleotide conjugate according to claim 2, wherein the end of the oligonucleotide strand and the molecule capable of binding to an asialoglycoprotein receptor are bound via a linker, the linker comprises a main chain linker that binds to the end of the oligonucleotide strand, and a side chain linker that branches from the main chain and binds to the molecule capable of binding to an asialoglycoprotein receptor, the main chain linker is a straight chain carbon chain selected from the group consisting of ethylene chain, propylene chain, butylene chain, pentylene chain, hexylene chain, heptylene chain, octylene chain, nonylene chain, decylene chain, dodecylene chain, tetradecylene chain, hexadecylene chain, and octadecylene chain (provided that when the side chain linker comprises a hetero atom, it optionally forms a heterocyclic ring together with a carbon atom of the main chain), and wherein the end of the oligonucleotide and the main chain linker, and, when two or more molecules capable of binding to asialoglycoprotein receptors are added, further the main chain linkers, are linked by phosphodiester bonds.

4. A pharmaceutical composition for inhibiting APOC3 protein expression, comprising the antisense oligomer, pharmaceutically acceptable salt thereof or pharmaceutically acceptable hydrate thereof according to claim 1.

5. A method for treating hypertriglyceridemia in a subject, comprising administering to the subject an effective amount of the antisense oligomer, pharmaceutically acceptable salt thereof or pharmaceutically acceptable hydrate thereof according to claim 1.

6. A method for treating primary hyperchylomicronemia in a subject, comprising administering to the subject an effective amount of the antisense oligomer, pharmaceutically acceptable salt thereof or pharmaceutically acceptable hydrate thereof according to claim 1.

7. A method for inhibiting APOC3 protein expression in a subject, comprising administering to the subject an effective amount of the oligonucleotide conjugate according to claim 2.

8. A method for treating hypertriglyceridemia in a subject, comprising administering to the subject an effective amount of the oligonucleotide conjugate according to claim 2.

9. A method for treating for primary hyperchylomicronemia in a subject, comprising administering to the subject an effective amount of the oligonucleotide conjugate according to claim 2.

10. A method for inhibiting APOC3 protein expression in a subject, comprising administering to the subject an effective amount of the antisense oligomer, pharmaceutically acceptable salt thereof or pharmaceutically acceptable hydrate thereof according to claim 1.

* * * * *

SEQUENCE LISTING

<160> NUMBER OF SEQ ID NOS: 41

<210> SEQ ID NO 1
<211> LENGTH: 14
<212> TYPE: DNA
<213> ORGANISM: Artificial Sequence
<220> FEATURE:
<223> OTHER INFORMATION: Antisense oligonucleotide against APOC3 mRMA

<400> SEQUENCE: 1
gggatgaact gagc 14

<210> SEQ ID NO 2
<211> LENGTH: 14
<212> TYPE: DNA
<213> ORGANISM: Artificial Sequence
<220> FEATURE:
<223> OTHER INFORMATION: Antisense oligonucleotide against APOC3 mRMA

<400> SEQUENCE: 2
gctgcctcta ggga 14

<210> SEQ ID NO 3
<211> LENGTH: 14
<212> TYPE: DNA
<213> ORGANISM: Artificial Sequence
<220> FEATURE:
<223> OTHER INFORMATION: Antisense oligonucleotide against APOC3 mRMA

<400> SEQUENCE: 3
gcacctctgt tcct 14

<210> SEQ ID NO 4
<211> LENGTH: 14
<212> TYPE: DNA
<213> ORGANISM: Artificial Sequence
<220> FEATURE:

<223> OTHER INFORMATION: Antisense oligonucleotide against APOC3 mRMA

<400> SEQUENCE: 4
aacaaggagt accc 14

<210> SEQ ID NO 5
<211> LENGTH: 14
<212> TYPE: DNA
<213> ORGANISM: Artificial Sequence
<220> FEATURE:
<223> OTHER INFORMATION: Antisense oligonucleotide against APOC3 mRMA

<400> SEQUENCE: 5
ggagggcaac aaca 14

<210> SEQ ID NO 6
<211> LENGTH: 14
<212> TYPE: DNA
<213> ORGANISM: Artificial Sequence
<220> FEATURE:
<223> OTHER INFORMATION: Antisense oligonucleotide against APOC3 mRMA

<400> SEQUENCE: 6
aagggaggca tcct 14

<210> SEQ ID NO 7
<211> LENGTH: 14
<212> TYPE: DNA
<213> ORGANISM: Artificial Sequence
<220> FEATURE:
<223> OTHER INFORMATION: Antisense oligonucleotide against APOC3 mRMA

<400> SEQUENCE: 7
taaccctgca tgaa 14

<210> SEQ ID NO 8
<211> LENGTH: 14
<212> TYPE: DNA
<213> ORGANISM: Artificial Sequence
<220> FEATURE:
<223> OTHER INFORMATION: Antisense oligonucleotide against APOC3 mRMA

<400> SEQUENCE: 8
gggccacctg ggac 14

<210> SEQ ID NO 9
<211> LENGTH: 14
<212> TYPE: DNA
<213> ORGANISM: Artificial Sequence
<220> FEATURE:
<223> OTHER INFORMATION: Antisense oligonucleotide against APOC3 mRMA

<400> SEQUENCE: 9
actgaagcca tcgg 14

<210> SEQ ID NO 10
<211> LENGTH: 14
<212> TYPE: DNA
<213> ORGANISM: Artificial Sequence
<220> FEATURE:
<223> OTHER INFORMATION: Antisense oligonucleotide against APOC3 mRMA

<400> SEQUENCE: 10
ctttcaggga actg 14

-continued

<210> SEQ ID NO 11
<211> LENGTH: 14
<212> TYPE: DNA
<213> ORGANISM: Artificial Sequence
<220> FEATURE:
<223> OTHER INFORMATION: Antisense oligonucleotide against APOC3 mRMA

<400> SEQUENCE: 11
ctccagtagt cttt 14

<210> SEQ ID NO 12
<211> LENGTH: 14
<212> TYPE: DNA
<213> ORGANISM: Artificial Sequence
<220> FEATURE:
<223> OTHER INFORMATION: Antisense oligonucleotide against APOC3 mRMA

<400> SEQUENCE: 12
ctcagagaac ttgt 14

<210> SEQ ID NO 13
<211> LENGTH: 14
<212> TYPE: DNA
<213> ORGANISM: Artificial Sequence
<220> FEATURE:
<223> OTHER INFORMATION: Antisense oligonucleotide against APOC3 mRMA

<400> SEQUENCE: 13
cagaactcag agaa 14

<210> SEQ ID NO 14
<211> LENGTH: 14
<212> TYPE: DNA
<213> ORGANISM: Artificial Sequence
<220> FEATURE:
<223> OTHER INFORMATION: Antisense oligonucleotide against APOC3 mRMA

<400> SEQUENCE: 14
tcagggtcca aatc 14

<210> SEQ ID NO 15
<211> LENGTH: 14
<212> TYPE: DNA
<213> ORGANISM: Artificial Sequence
<220> FEATURE:
<223> OTHER INFORMATION: Antisense oligonucleotide against APOC3 mRMA

<400> SEQUENCE: 15
tgacctcagg gtcc 14

<210> SEQ ID NO 16
<211> LENGTH: 14
<212> TYPE: DNA
<213> ORGANISM: Artificial Sequence
<220> FEATURE:
<223> OTHER INFORMATION: Antisense oligonucleotide against APOC3 mRMA

<400> SEQUENCE: 16
tggtctgacc tcag 14

<210> SEQ ID NO 17
<211> LENGTH: 14
<212> TYPE: DNA
<213> ORGANISM: Artificial Sequence
<220> FEATURE:
<223> OTHER INFORMATION: Antisense oligonucleotide against APOC3 mRMA -continued

<400> SEQUENCE: 17
gaagttggtc tgac 14

<210> SEQ ID NO 18
<211> LENGTH: 14
<212> TYPE: DNA
<213> ORGANISM: Artificial Sequence
<220> FEATURE:
<223> OTHER INFORMATION: Antisense oligonucleotide against APOC3 mRMA

<400> SEQUENCE: 18
caggcagcca cggc 14

<210> SEQ ID NO 19
<211> LENGTH: 14
<212> TYPE: DNA
<213> ORGANISM: Artificial Sequence
<220> FEATURE:
<223> OTHER INFORMATION: Antisense oligonucleotide against APOC3 mRMA

<400> SEQUENCE: 19
ggtctcaggc agcc 14

<210> SEQ ID NO 20
<211> LENGTH: 14
<212> TYPE: DNA
<213> ORGANISM: Artificial Sequence
<220> FEATURE:
<223> OTHER INFORMATION: Antisense oligonucleotide against APOC3 mRMA

<400> SEQUENCE: 20
attgaggtct cagg 14

<210> SEQ ID NO 21
<211> LENGTH: 14
<212> TYPE: DNA
<213> ORGANISM: Artificial Sequence
<220> FEATURE:
<223> OTHER INFORMATION: Antisense oligonucleotide against APOC3 mRMA

<400> SEQUENCE: 21
ggggtattga ggtc 14

<210> SEQ ID NO 22
<211> LENGTH: 14
<212> TYPE: DNA
<213> ORGANISM: Artificial Sequence
<220> FEATURE:
<223> OTHER INFORMATION: Antisense oligonucleotide against APOC3 mRMA

<400> SEQUENCE: 22
taggcaggtg gact 14

<210> SEQ ID NO 23
<211> LENGTH: 14
<212> TYPE: DNA
<213> ORGANISM: Artificial Sequence
<220> FEATURE:
<223> OTHER INFORMATION: Antisense oligonucleotide against APOC3 mRMA

<400> SEQUENCE: 23
atggataggc aggt 14

<210> SEQ ID NO 24
<211> LENGTH: 14

-continued

<212> TYPE: DNA
<213> ORGANISM: Artificial Sequence
<220> FEATURE:
<223> OTHER INFORMATION: Antisense oligonucleotide against APOC3 mRMA

<400> SEQUENCE: 24
ttgcaggacc caag 14

<210> SEQ ID NO 25
<211> LENGTH: 14
<212> TYPE: DNA
<213> ORGANISM: Artificial Sequence
<220> FEATURE:
<223> OTHER INFORMATION: Antisense oligonucleotide against APOC3 mRMA

<400> SEQUENCE: 25
ttaagcaacc taca 14

<210> SEQ ID NO 26
<211> LENGTH: 14
<212> TYPE: DNA
<213> ORGANISM: Artificial Sequence
<220> FEATURE:
<223> OTHER INFORMATION: Antisense oligonucleotide against APOC3 mRMA

<400> SEQUENCE: 26
agaatactgt ccct 14

<210> SEQ ID NO 27
<211> LENGTH: 14
<212> TYPE: DNA
<213> ORGANISM: Artificial Sequence
<220> FEATURE:
<223> OTHER INFORMATION: Antisense oligonucleotide against APOC3 mRMA

<400> SEQUENCE: 27
cactgagaat actg 14

<210> SEQ ID NO 28
<211> LENGTH: 14
<212> TYPE: DNA
<213> ORGANISM: Artificial Sequence
<220> FEATURE:
<223> OTHER INFORMATION: Antisense oligonucleotide against APOC3 mRMA

<400> SEQUENCE: 28
gagagcactg agaa 14

<210> SEQ ID NO 29
<211> LENGTH: 14
<212> TYPE: DNA
<213> ORGANISM: Artificial Sequence
<220> FEATURE:
<223> OTHER INFORMATION: Antisense oligonucleotide against APOC3 mRMA

<400> SEQUENCE: 29
ggaggccagc atgc 14

<210> SEQ ID NO 30
<211> LENGTH: 14
<212> TYPE: DNA
<213> ORGANISM: Artificial Sequence
<220> FEATURE:
<223> OTHER INFORMATION: Antisense oligonucleotide against APOC3 mRMA

<400> SEQUENCE: 30

-continued

```
tattgggagg ccag                                                     14


<210> SEQ ID NO 31
<211> LENGTH: 14
<212> TYPE: DNA
<213> ORGANISM: Artificial Sequence
<220> FEATURE:
<223> OTHER INFORMATION: Antisense oligonucleotide against APOC3 mRMA

<400> SEQUENCE: 31

agctttattg ggag                                                     14


<210> SEQ ID NO 32
<211> LENGTH: 14
<212> TYPE: DNA
<213> ORGANISM: Artificial Sequence
<220> FEATURE:
<223> OTHER INFORMATION: Antisense oligonucleotide against APOC3 mRMA

<400> SEQUENCE: 32

cttcttgtcc agct                                                     14


<210> SEQ ID NO 33
<211> LENGTH: 535
<212> TYPE: DNA
<213> ORGANISM: Homo sapiens
<220> FEATURE:
<221> NAME/KEY: CDS
<222> LOCATION: (48)..(347)

<400> SEQUENCE: 33

ctgctcagtt catccctaga ggcagctgct ccaggaacag aggtgcc atg cag ccc       56
                                                    Met Gln Pro
                                                    1

cgg gta ctc ctt gtt gtt gcc ctc ctg gcg ctc ctg gcc tct gcc cga      104
Arg Val Leu Leu Val Val Ala Leu Leu Ala Leu Leu Ala Ser Ala Arg
    5                   10                  15

gct tca gag gcc gag gat gcc tcc ctt ctc agc ttc atg cag ggt tac      152
Ala Ser Glu Ala Glu Asp Ala Ser Leu Leu Ser Phe Met Gln Gly Tyr
20                  25                  30                  35

atg aag cac gcc acc aag acc gcc aag gat gca ctg agc agc gtg cag      200
Met Lys His Ala Thr Lys Thr Ala Lys Asp Ala Leu Ser Ser Val Gln
                40                  45                  50

gag tcc cag gtg gcc cag cag gcc agg ggc tgg gtg acc gat ggc ttc      248
Glu Ser Gln Val Ala Gln Gln Ala Arg Gly Trp Val Thr Asp Gly Phe
            55                  60                  65

agt tcc ctg aaa gac tac tgg agc acc gtt aag gac aag ttc tct gag      296
Ser Ser Leu Lys Asp Tyr Trp Ser Thr Val Lys Asp Lys Phe Ser Glu
        70                  75                  80

ttc tgg gat ttg gac cct gag gtc aga cca act tca gcc gtg gct gcc      344
Phe Trp Asp Leu Asp Pro Glu Val Arg Pro Thr Ser Ala Val Ala Ala
    85                  90                  95

tga gacctcaata ccccaagtcc acctgcctat ccatcctgcg agctccttgg           397

gtcctgcaat ctccagggct gcccctgtag gttgcttaaa agggacagta ttctcagtgc    457

tctcctaccc cacctcatgc ctggcccccc tccaggcatg ctggcctccc aataaagctg    517

gacaagaagc tgctatga                                                  535


<210> SEQ ID NO 34
<211> LENGTH: 99
<212> TYPE: PRT
<213> ORGANISM: Homo sapiens
```

-continued

<400> SEQUENCE: 34

```
Met Gln Pro Arg Val Leu Leu Val Val Ala Leu Leu Ala Leu Leu Ala
1               5                   10                  15

Ser Ala Arg Ala Ser Glu Ala Glu Asp Ala Ser Leu Leu Ser Phe Met
            20                  25                  30

Gln Gly Tyr Met Lys His Ala Thr Lys Thr Ala Lys Asp Ala Leu Ser
        35                  40                  45

Ser Val Gln Glu Ser Gln Val Ala Gln Gln Ala Arg Gly Trp Val Thr
    50                  55                  60

Asp Gly Phe Ser Ser Leu Lys Asp Tyr Trp Ser Thr Val Lys Asp Lys
65                  70                  75                  80

Phe Ser Glu Phe Trp Asp Leu Asp Pro Glu Val Arg Pro Thr Ser Ala
                85                  90                  95

Val Ala Ala
```

<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35
gcaccgtcaa ggctgagaac 20

<210> SEQ ID NO 36
<211> LENGTH: 19
<212> TYPE: DNA
<213> ORGANISM: Artificial Sequence
<220> FEATURE:
<223> OTHER INFORMATION: Primer

<400> SEQUENCE: 36
tggtgaagac gccagtgga 19

<210> SEQ ID NO 37
<211> LENGTH: 16
<212> TYPE: DNA
<213> ORGANISM: Artificial Sequence
<220> FEATURE:
<223> OTHER INFORMATION: Antisense oligonucleotide against APOC3 mRMA

<400> SEQUENCE: 37
tgagaatact gtccct 16

<210> SEQ ID NO 38
<211> LENGTH: 15
<212> TYPE: DNA
<213> ORGANISM: Artificial Sequence
<220> FEATURE:
<223> OTHER INFORMATION: Antisense oligonucleotide against APOC3 mRMA

<400> SEQUENCE: 38
gagaatactg tccct 15

<210> SEQ ID NO 39
<211> LENGTH: 15
<212> TYPE: DNA
<213> ORGANISM: Artificial Sequence
<220> FEATURE:
<223> OTHER INFORMATION: Antisense oligonucleotide against APOC3 mRMA

<400> SEQUENCE: 39

-continued

```
agaatactgt ccctt                                                      15


<210> SEQ ID NO 40
<211> LENGTH: 17
<212> TYPE: DNA
<213> ORGANISM: Artificial Sequence
<220> FEATURE:
<223> OTHER INFORMATION: Antisense oligonucleotide against APOC3 mRMA

<400> SEQUENCE: 40

tgagaatact gtccctt                                                    17


<210> SEQ ID NO 41
<211> LENGTH: 20
<212> TYPE: DNA
<213> ORGANISM: Artificial Sequence
<220> FEATURE:
<223> OTHER INFORMATION: Antisense oligonucleotide against APOC3 mRMA

<400> SEQUENCE: 41

actgagaata ctgtcccttt                                                 20
```